US007932054B2

(12) United States Patent
Adney et al.

(10) Patent No.: US 7,932,054 B2
(45) Date of Patent: Apr. 26, 2011

(54) **METHODS OF USING THERMAL TOLERANT AVICELASE FROM *ACIDOTHERMUS CELLULOLYTICUS***

(75) Inventors: William S. Adney, Golden, CO (US);
Todd B. Vinzant, Golden, CO (US);
Shih-You Ding, Golden, CO (US);
Michael E. Himmel, Golden, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 12/425,299

(22) Filed: Apr. 16, 2009

(65) Prior Publication Data

US 2010/0136667 A1   Jun. 3, 2010

Related U.S. Application Data

(62) Division of application No. 10/155,400, filed on Oct. 18, 2002, now Pat. No. 7,538,200, which is a division of application No. 09/917,376, filed on Jul. 28, 2001, now Pat. No. 7,364,890.

(51) Int. Cl.
*C12P 21/00* (2006.01)
*A23B 7/10* (2006.01)
*A23K 1/00* (2006.01)
*A23K 3/00* (2006.01)

(52) U.S. Cl. ............................ 435/68.1; 426/53; 426/54
(58) Field of Classification Search ........................ None
See application file for complete search history.

(56) References Cited

U.S. PATENT DOCUMENTS

| | | | |
|---|---|---|---|
| 4,518,584 A | 5/1985 | Mark et al. |
| 4,737,462 A | 4/1988 | Mark et al. |
| 5,110,735 A | 5/1992 | Tucker et al. |
| 5,120,463 A | 6/1992 | Bjork et al. |
| 5,272,071 A | 12/1993 | Chappel |
| 5,275,944 A | 1/1994 | Himmel et al. |
| 5,326,562 A | 7/1994 | Scott |
| 5,366,884 A | 11/1994 | Adney et al. |
| 5,432,075 A | 7/1995 | Himmel et al. |
| 5,514,584 A | 5/1996 | Lastick et al. |
| 5,536,655 A | 7/1996 | Thomas et al. |
| 5,712,142 A | 1/1998 | Adney et al. |
| 5,908,472 A | 6/1999 | Vollmond |
| 5,965,408 A | 10/1999 | Short |
| 6,013,860 A | 1/2000 | Himmel et al. |
| 6,126,698 A | 10/2000 | Liu et al. |
| 6,582,908 B2 | 6/2003 | Fodor et al. |
| 7,112,429 B2 | 9/2006 | Ding et al. |
| 7,364,890 B2 | 4/2008 | Ding et al. |
| 7,538,200 B2 | 5/2009 | Ding et al. |

FOREIGN PATENT DOCUMENTS

WO   97/07203   2/1997
WO   99/31241   6/1999

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Al-Sulami, et al. "Purification and Properties of Cellulases from a Local Isolate of *Cellulomonas flavigena*." Dirasat, 1992, vol. 19B, No. 4, pp. 139-155 (Univ. Jordan).
Arai, et al., "Avicelase III from *Aspergillus aculeatus*", Database EMBL 'Online' 1 Accession No. 074170, Abstract.
Ausbel, et al., "Affinity Purification of Proteins Binding to GST Fusion Proteins", Current Protocols In Molecular Biology, 1996, Chapter 20, Unit 20.2 Wiley, 2 pages.
Author Unknown, "Expression and Purification of GST Fusion Proteins", Current Protocols in Protein Science, 2002, Chapter 6, Unit 6.6, John Wiley & Sons.
Baker, et al., "Synergism Between Purified Bacterial and Fungal Cellulases", Journal of the American Chemical Society Symposium Series, 1996, vol. 618, Chapter 9, pp. 113-141.
Baker, et al., "A New Thermostable Endoglucanase, *Acidothemus cellulolyticus* E1", Applied Biochemistry and Biotechnology, 1994, vol. 45/46, pp. 245-256.
Bergem, et al., "The mechanism of enzymatic cellulose degradation. Purification and some properties of two different 1,4-β-glucan glucanohydrolases from *Trichoderma viride*", European journal of biochemistry / FEBS, Jan. 15, 1976, vol. 61, No. 2, pp. 621-630.
Bronnenmeir, et al., "Purification and properties of a novel type of exo-1,4-β-glucanase (Avicelase II) from the cellulolytic thermophile *Clostridium stercorarium*",European Journal of Biochemistry / FEBS, Sep. 1, 1991, vol. 200, pp. 379-385.
Gal, et al., "CelG from *Clostridium cellulolyticum*: a Multidomain Endoglucanase Acting Efficiently on Crystalline Cellulose", Journal of Bacteriology, Nov. 1997, vol. 179, No. 21, pp. 6595-6601.
Galye, et al, "Identification of regions in interleukin-1α important for activity", The Journal of Biological Chemistry, Oct. 15, 1993, vol. 268, No. 29, pp. 22105-22111. Gilkes, et al., "Precise Excision of the Cellulose Binding Domains from Two Cellulomonas fimi Cellulases by a Homologous Protease and the Effect on Catalysis", The Journal of Biological Chemistry, Jul. 25, 1988 vol. 263, No. 21, pp. 10401-10407.
Gou, et al., "Protein tolerance to random amino acid change",Proceedings of the National Academy of Sciences of the United States of America, Jun. 22, 2004, vol. 101, No. 25, pp. 9205-9210.
Hanks, et al., "Protein Kinase Catalytic Domain Sequence Database: Identification of Conserved Features of Primary Structure and Classification of Family Members",Methods Enzymology,1991 vol. 200, pp. 38-62.
Harrison, et al., "Modified glycosylation of cellobiohydrolase I from a high cellulase-producing mutant strain of *Trichoderma reesei*", European Journal of Biochemistry / FEBS, Aug. 15, 1998, vol. 256, No. 1, pp. 119-127.
Hasper, et al., "EgIC, A New Endoglucanase from *Aspergillus niger* with Major Activitytowards Xyloglucan", Applied & Environmental Microbiology, Apr. 2002, vol. 68, No. 4, pp. 1556-1560.

(Continued)

*Primary Examiner* — Sheridan Swope
(74) *Attorney, Agent, or Firm* — Paul J. White; John C. Stolpa; W. LaNelle Owens

(57) ABSTRACT

The invention provides a thermal tolerant (thermostable) cellulase, AvilII, that is a member of the glycoside hydrolase (GH) family. AvilII was isolated and characterized from *Acidothermus cellulolyticus*, and, like many cellulases, the disclosed polypeptide and/or its derivatives may be useful for the conversion of biomass into biofuels and chemicals.

16 Claims, 2 Drawing Sheets

OTHER PUBLICATIONS

Henrissat, "A classification of glycosyl hydrolses based on aminoacid sequence similarities", Biochem. J., 1999, vol. 280, pp. 309-316.

Jun, et al., "Lune/eye gone, a Pax-like protein, uses a partial paired domain and a homeodomain for DNA recognition", Proceedings of the National Academy of Sciences of the United States of America, Nov. 1998, vol, 95, pp. 13720-13725.

Katz, et al., "Production of Glucose by Enzymatic Hydrolysis of Cellulose", Applied Microbiology, Feb. 1968, vol. 16, No. 2, pp. 419-420.

Klarskov, et al., "Cellobiohydrolase I from *Trichoderma reesei*: Identification of an active-site nucleophile andadditional information on sequence including the glycosylation pattern of the core protein", Carbohydrate Research, Nov. 10, 1997, vol. 304, No. 2, pp. 143-154.

Mandels, et al., "The Production of Cellulases", Cellulases and Their Applications, Advanced Chemical Services, 1969, vol. 95, pp. 391-414.

Mohagheghi, et al., "Isolation and Characterization of *Acidothermus cellulolyticus* gen. nov., sp. nov., a New Genus of Thermophilic, Acidophilic Cellulolytic Bacteria", International Journal of Systematic Bacteriology, Jul. 1986, vol. 36, No. 3, pp. 435-443.

Pauly, et al, "A xyloglucan-specific endo-B-1,4-grucanase from *Aspergillus aculeatus*: expression cloning in yeast, purification and characterization of the recombinant enzyme", Glycobiology,1999, vol. 9, No. 1, pp. 93-100.

Pauly, et al., "In house BLAST alignment of SED ID No: 3 with AF043595", Glycobiology, Jan. 1999, vol. 9, No. 1, pp. 93-100.

Robson, et al., "Endoglucanase Precursor (EC 3.2.1.4) (ENDO-1, 4-β-Glucanase) (Cellulase)," XP002195539.

Robson, et al., "Endo-β-1, 4-Glucanase Gene of *Bacillus subtilis* DLG," Journal of Bacteriology, May 1, 1987, vol. 169, No. 5, pp. 1801-1806.

Seeger, et al., PIR database Accession No. T35237, Nov. 5, 1999, Alignment with SEQ ID No. 1.

Takada, et al, "Cloning & Transportation Analysis of the *Aspergillus aculeatus* No. F-50 Endoglucanase 2 (cmc2)", Gene, 2002, Journal of Bioscience and Bioengineering, vol. 94, No. 5, pp. 482-485.

Tan, et al., "Column cellulose hydrolysis reactor: Cellulas adsorption profile", Applied Microbiology Biotechnology, 1986, vol. 25, pp. 256-261.

Tatusova, et al, "BLAST 2 Sequences, a new tool for comparing protein and nucleotide sequences", FEMS Microbiology Letters, May 15, 1999, vol. 174, No. 2, pp. 247-250: Erratum in: FEMS Microbiol Letters, Aug. 1, 1999, vol. 177, No. 1, pp. 187-188.

Tomme, et al., "Characterization and affinity applications of cellulose-binding domains", Journal of Chromatography B: Biomedical Sciences and Applications, Sep. 11, 1998, vol. 175, No. pp. 283-296.

Tormo, et al, Crystal structure of a bacterial family-III cellulose-binding domain: a genderal mechanism for attachment to cellulose, The EMBO Journal, Nov. 1996, vol. 15, No. 21, pp. 5739-5751.

Tucker, et al., "Ultra-Thermostable Cellulase from *Acidothermus celluloyticus*: Comparison with Previously Reported Cellulases", Bio/ Technology, 1989, vol. 7, No. 8, pp. 817-820.

Whisstock, et al., "Prediction of protein function from protein sequence and structure", Quarterly reviews of Biophysics, Aug. 2003, vol. 36, No. 36, pp. 307-340.

Wiselogel, et al., "Biomass feedstocks resources and composition—in CE", Handbook on Bioethanol: Production and Utilization, 1996, pp. 105-118 Washington, DC; Taylor & Francis.

Table 2;.amendment to the instant Application, U.S. Appl. No. 10/155,400, filed Mar. 1, 2007, p. 3.

Bhat, et al, "Cellulose degrading enzymes and their potential industrial applications", Biotechnology Advances,1997, vol. 15, Nos. 3-4, pp. 583-620.

Gibbs, et al., "Multidomain and multfunctional Glycosyl hydrolases from the extreme Thermophile Caldicelluosiruptor isolate Tok7B.1," Current Microbiology, 2000, vol. 40. No. 5, pp. 333-340.

Irwin, et al., "Roles of the catalytic domain and two cellulose binding domains of *Thermomonospora fusca* E4 in cellulose hydrolysis", J. Bacteriology, Apr. 1998, vol. 180, No. 7, pp. 1709-1714.

Gibbs, et al., "Glycosyl hydrolases 5 (Caldicelluosiruptor sp.Tok7B. 1," Database EMBL 'Online'! Accession No. AAK06388, Abstract.

International Search Report for International (PCT) Application No. PCT/US01/23818, mailed Apr. 18, 2002.

Altschul, et al., "Basic local alignment search tool", Oct. 5, 1990, Journal of Molecular Biology, vol. 215, No. 3, pp. 403-410.

Arnold, "When blind is better: Protein design by evolution", Jul. 1998, Nature Biotechnology, vol. 16, No. 7, pp. 617-618.

Author Unknown, iupac-iubmb Joint Commission on Biochemical Nomenclature (JCBN) and Nomenclature Committee of IUBMB (NC-IUBMB), European Journal of Biochemistry—FEBS, 1999, vol. 264, pp. 607-609.

Baird, et al., "Molecular cloning, expression, and characterization of endo-beta-1,4-glucanase genes from *Bacillus polymyxa* and *Bacillus circulans*", Journal of Bacteriology, Mar. 1990, vol. 172, No. 3, pp. 1576-1586.

Bauer, et al., "A genetic enrichment for mutations constructed by oligodeoxynucleotide-directed mutagenesis", Gene, 1985, vol. 37, Nos. 1-3, pp. 73-81.

Bergeron, "Environmental impacts of bioethanol", Handbook on Bioethanol: Production and Utilization, 1996, Taylor & Francis, Chapter 5, pp. 90-103, Washington, DC.

Bowie, et al., "Deciphering the message in protein sequences; tolerance to amino acid substitutions", Science, Mar. 16, 1990, vol. 247, No. 4948, pp. 1306-1310.

Colbère-Garapin, et al., "A new dominant hybrid selective marker for higher eukaryotic cells", Journal of Molecular Biology, Jul. 25, 1981, vol. 150, No. 1, pp. 1-14.

Cosman, et al., "ULBPs novel MHC class I-related molecules, bind to CMV glycoprotein UL16 and stimulate NK cytotoxicity through the NKG2D receptor", Immunity, Feb. 2001, vol. 14, No. 2, pp. 123-133.

Cowan, "Enzymes from thermophilic archaebacteria: current and future applications in biotechnology", Biochemical Society Symposia: The Archaebacteria: Biochemistry andBiotechnology, Oct. 1992, vol. 58, pp. 149-159, Edited by MJ Dawson, DW Danson and GG Lunt, Portland Press.

Craik, "Use of Oligonucleotides for Site-Specific Mutagenesis", BioTechniques, Jan./Feb. 1935, vol. 3, pp. 12-19.

Crameri et al., "DNA Shufflino of a family of genes from diverse species accelerates directed evolution", Nature, Jan. 1998, vol. 391, pp. 288-291.

Dai, et al., "Expression of *Acidothermus cellulolyticus* endoglucanase E1 in transgenic tobacco: biochemical characteristics and physiological effects", Transgenic Research, 2000, vol. 9, No. 1, pp. 43-54.

Deacon, "Cellulose decomposition: a case study of extracellular enzymes", Modern Mycology, Chapter 5, 3rd Ed., pp. 97-98, Blackwell Science.

Gough, et al., "Nucleotide sequence of the engXCA gene encoding the major endoglucanase of *Xanthomonas campestris* pv. *Campestris*", Gene, Apr. 30, 1990, vol. 89, No. 1, pp. 53-59.

Graham, et al., "Manipulation of Adenovirus Vectors", Gene Transfer and Expression Protocols, From: Methods in Molecular Biology, Chapter 11, Apr. 22, 1991, vol. 7, pp. 109-128.

Hansen, et al., "celA from *Bacillus lautus* PL236 Encodes a Novel Cellulose-Binding Endo-β-1,4-Glucanase", Journal of Bacteriology Bacteriol. Jun. 1992, vol. 174, No. 11, pp. 3522-3531.

Hellinga, "Computational Engineering", Nature Structural and Molecular Biology, Jul. 1998, vol. 5, No. 7, pp. 525-527.

Henrissat, et al., "Updating the sequence-based classification of glycosyl hydrolases", The Biochemical Journal, Jun. 1, 1996, vol. 316, Part 2, pp. 695-696.

Kao, et al., "Genetics of somatic mammalian cells, VII. Induction and isolation of nutritional mutants in Chinese hamster cells", Proceedings of the National Academy of Sciences of the United States of America, Aug. 1968 vol. 60, No. 4, pp. 1275-1281.

Koivula, et al., "Immunoaffinity Chromatographic Purification of Cellobiohydrolase II Mutants from Recombinant *Trichoderma reesei* Strains Devoid of Major Endoglucanase Genes", Protein Expression and Purification, 1996, vol. 8, pp. 391-400.

Landschultz, at al., "The leucine zipper: a hypothetical structure common to a new class of DNA binding proteins", Science, Jun. 24, 1988, vol. 240, No. 4860. pp. 1759.

Luckow, et al., "Trends in the Development of Bacuiovirus Expression Vectors", Bio-Technology, Jan. 1988, vol. 6, pp. 47-55.

Mulligan, et al., "Selection for animal cells that express the *Escherichia coli* gene coding for xanthine-guanine phosphoribosyltransferase", Proceedings of the National Academy of Sciences of the United States of America. Apr. 1981, vol. 78, No. 4, pp. 2072-2076.

O'Hare., et al., "Transformation of mouse fibroblasts to methotrexate resistance by a recombinant plasmid expressing a prokaryotic dihydrofolate reductase", Proceedings of the National Academy of Sciences of the United States of America, Mar. 1981, vol. 78, No. 3, pp. 1527-1531.

Santerre, et al., "Expression of prokaryotic genes for hygromycin B and G418 resistance as dominant-selection marker in mouse L cells", Gene, Oct. 1984, vol. 30, Nos. 1-3, pp. 147-156.

Segal., et al., "Toward controlling gene expression at will: selection and design of zinc finger domains recognizing each of the 5'-GNN-3' DNA target sequences", Proceedings of the National Academy of Sciences of the United States of America, Mar. 16, 1999, vol. 96, No. 6, pp. 2758-2763.

Sihorkar, et al. "Potential of polysaccharide anchored liposomes in drugs delivery, targeting and immunization"; J. Pharmacy & Pharmaceutical Sciences, 2001, vol. 4, No. 2, pp. 138-158.

Smith, et al., "Comparison of biosequences", Advances in Applied Mathematics, Dec. 1981, vol. 2, No. 4, pp. 482-489.

Summers, et al., "A Manual of Methods for Baculovirus Vectors and Insect Cell Culture Procedures", Texas Agricultural Experiment Station, 1987, Bulletin No. 1555, pp. 1-56, College Station, Texas.

Thompson, et al., "Clustal W: Improving the sensitivity of progressive multiple sequence alignment through sequence weighting, position-specific gap penalties and weight matrix cholce",Nucleic Acids Research, Nov. 11, 1994, vol. 22, No. 22, pp. 4676-4680.

Tipton, et al., "Nomenclature Commitee of the International Union of Biochemistry and Molecular Biology (NC-IUBMB)", European Journal of Biochemistry-FEBS, 1999, vol. 264, Enzyme Supplement 5, pp. 610-650.

Tomme, et al., "Celluiose-Binding Domains: Classification and Properties", Enzymatic Degradation of Insoluble Carbohydrates, May 5, 1996, Chapter 10, pp. 142-163, Saddler JN & Penner M, eds., American Chemical Society Washington.

Tomme, et al., "Identification of a functionally important carboxyl group in cellobiohydrolase I from *Trichoderma reesei*: A chemical modification study", FEBS Letters, Jan. 30, 1989, vol. 243, No. 2, pp. 239-243.

Van Den Burg, et al., "Engineering an enzyme to resist boiling", Proceedings of the National Academy of Sciences of the United States of America, Mar. 3, 1998, vol. 95, No. 5, pp. 2056-2060.

Walder, et al., "Oligodeoxynucleotide-directed mutagenesis using the yeast transformation system", Gene, 1986, vol. 42, No. 2, pp. 133-139.

Wigler, et. al, "Transformation of mammalian cells with an amplifiable dominant-acting gene", Proceedings of the National Academy of Sciences of the United States of America, Jun. 1980, vol. 77, No. 6, pp. 3567-3570.

Wiselogel, et al., "Biomass Feedstock Resources and Composition", Handbook on Bioethanol: Production and Utilization, Chapter 6, 1996, pp. 105-118, Washington, D.C.

Zhau, et al., "Molecular evolution by staggered extension process (StEP) in vitro recombination", Nature Biotechnology, 1998, vol. 16, No. 3, pp. 258-262.

Official Action for U.S. Appl. No. 09/917,376, mailed May 18, 2007.
Official Action for U.S. Appl. No. 09/917,376, mailed Apr. 18, 2006.
Official Action for U.S. Appl. No. 09/917,376, mailed Nov. 8, 2005.
Official Action for U.S. Appl. No. 09/917,376, mailed May 18, 2005.
Official Action for U.S. Appl. No. 09/917,376, mailed Jun. 16, 2004.
Official Action for U.S. Appl. No. 09/917,376, mailed Jan. 16, 2004.
Official Action for U.S. Appl. No. 09/917,376, mailed Mar. 11, 2003.
Official Action for U.S. Appl. No. 09/917,376, mailed Aug. 1, 2002.
Official Action for U.S. Appl. No. 10/155,400, mailed Sep. 16, 2003.
Official Action for U.S. Appl. No. 10/155,400, mailed Nov. 5, 2003.
Official Action for U.S. Appl. No. 10/155,400, mailed Apr. 16, 2004.
Official Action for U.S. Appl. No. 10/155,400, mailed May 6, 2005.
Official Action for U.S. Appl. No. 10/155,400, mailed Mar. 2, 2006.
Official Action for U.S. Appl. No. 10/155,400, mailed May 18, 2007.
Official Action for U.S. Appl. No. 10/155,400, mailed Nov. 14, 2007.
Official Action for U.S. Appl. No. 10/155,400, mailed Jul. 16, 2008.

* cited by examiner

SEQUENCE LISTING

```
<160> NUMBER OF SEQ ID NOS: 8

<210> SEQ ID NO 1
<211> LENGTH: 957
<212> TYPE: PRT
<213> ORGANISM: Acidothermus cellulolyticus
<220> FEATURE:
<221> NAME/KEY: misc_feature
<222> LOCATION: (957)..(957)
<223> OTHER INFORMATION: Xaa can be any naturally occurring amino acid

<400> SEQUENCE: 1

Met Asp Arg Ser Glu Asn Ile Arg Leu Thr Met Arg Ser Arg Arg Leu
1               5                   10                  15

Val Ser Leu Leu Ala Ala Thr Ala Ser Phe Ala Val Ala Ala Ala Leu
                20                  25                  30

Gly Val Leu Pro Ile Ala Ile Thr Ala Ser Pro Ala His Ala Ala Thr
            35                  40                  45

Thr Gln Pro Tyr Thr Trp Ser Asn Val Ala Ile Gly Gly Gly Gly Phe
        50                  55                  60

Val Asp Gly Ile Val Phe Asn Glu Gly Ala Pro Gly Ile Leu Tyr Val
65                  70                  75                  80

Arg Thr Asp Ile Gly Gly Met Tyr Arg Trp Asp Ala Ala Asn Gly Arg
                85                  90                  95

Trp Ile Pro Leu Leu Asp Trp Val Gly Trp Asn Asn Trp Gly Tyr Asn
                100                 105                 110
```

```
Gly Val Val Ser Ile Ala Ala Asp Pro Ile Asn Thr Asn Lys Val Trp
            115                 120                 125

Ala Ala Val Gly Met Tyr Thr Asn Ser Trp Asp Pro Asn Asp Gly Ala
130                 135                 140

Ile Leu Arg Ser Ser Asp Gln Gly Ala Thr Trp Gln Ile Thr Pro Leu
145                 150                 155                 160

Pro Phe Lys Leu Gly Gly Asn Met Pro Gly Arg Gly Met Gly Glu Arg
                165                 170                 175

Leu Ala Val Asp Pro Asn Asn Asp Asn Ile Leu Tyr Phe Gly Ala Pro
            180                 185                 190

Ser Gly Lys Gly Leu Trp Arg Ser Thr Asp Ser Gly Ala Thr Trp Ser
        195                 200                 205

Gln Met Thr Asn Phe Pro Asp Val Gly Thr Tyr Ile Ala Asn Pro Thr
    210                 215                 220

Asp Thr Thr Gly Tyr Gln Ser Asp Ile Gln Gly Val Trp Val Ala
225                 230                 235                 240

Phe Asp Lys Ser Ser Ser Ser Leu Gly Gln Ala Ser Lys Thr Ile Phe
                245                 250                 255

Val Gly Val Ala Asp Pro Asn Asn Pro Val Phe Trp Ser Arg Asp Gly
            260                 265                 270

Gly Ala Thr Trp Gln Ala Val Pro Gly Ala Pro Thr Gly Phe Ile Pro
        275                 280                 285

His Lys Gly Val Phe Asp Pro Val Asn His Val Leu Tyr Ile Ala Thr
    290                 295                 300

Ser Asn Thr Gly Gly Pro Tyr Asp Gly Ser Ser Gly Asp Val Trp Lys
305                 310                 315                 320

Phe Ser Val Thr Ser Gly Thr Trp Thr Arg Ile Ser Pro Val Pro Ser
                325                 330                 335

Thr Asp Thr Ala Asn Asp Tyr Phe Gly Tyr Ser Gly Leu Thr Ile Asp
            340                 345                 350

Arg Gln His Pro Asn Thr Ile Met Val Ala Thr Gln Ile Ser Trp Trp
        355                 360                 365

Pro Asp Thr Ile Ile Phe Arg Ser Thr Asp Gly Gly Ala Thr Trp Thr
    370                 375                 380

Arg Ile Trp Asp Trp Thr Ser Tyr Pro Asn Arg Ser Leu Arg Tyr Val
385                 390                 395                 400

Leu Asp Ile Ser Ala Glu Pro Trp Leu Thr Phe Gly Val Gln Pro Asn
                405                 410                 415

Pro Pro Val Pro Ser Pro Lys Leu Gly Trp Met Asp Glu Ala Met Ala
            420                 425                 430

Ile Asp Pro Phe Asn Ser Asp Arg Met Leu Tyr Gly Thr Gly Ala Thr
        435                 440                 445

Leu Tyr Ala Thr Asn Asp Leu Thr Lys Trp Asp Ser Gly Gly Gln Ile
    450                 455                 460

His Ile Ala Pro Met Val Lys Gly Leu Glu Glu Thr Ala Val Asn Asp
465                 470                 475                 480

Leu Ile Ser Pro Pro Ser Gly Ala Pro Leu Ile Ser Ala Leu Gly Asp
                485                 490                 495

Leu Gly Gly Phe Thr His Ala Asp Val Thr Ala Val Pro Ser Thr Ile
            500                 505                 510

Phe Thr Ser Pro Val Phe Thr Thr Gly Thr Ser Val Asp Tyr Ala Glu
        515                 520                 525

Leu Asn Pro Ser Ile Ile Val Arg Ala Gly Ser Phe Asp Pro Ser Ser
```

```
                530                 535                 540
Gln Pro Asn Asp Arg His Val Ala Phe Ser Thr Asp Gly Gly Lys Asn
545                 550                 555                 560

Trp Phe Gln Gly Ser Glu Pro Gly Gly Val Thr Thr Gly Gly Thr Val
                565                 570                 575

Ala Ala Ser Ala Asp Gly Ser Arg Phe Val Trp Ala Pro Gly Asp Pro
                580                 585                 590

Gly Gln Pro Val Val Tyr Ala Val Gly Phe Gly Asn Ser Trp Ala Ala
            595                 600                 605

Ser Gln Gly Val Pro Ala Asn Ala Gln Ile Arg Ser Asp Arg Val Asn
        610                 615                 620

Pro Lys Thr Phe Tyr Ala Leu Ser Asn Gly Thr Phe Tyr Arg Ser Thr
625                 630                 635                 640

Asp Gly Gly Val Thr Phe Gln Pro Val Ala Gly Leu Pro Ser Ser
                645                 650                 655

Gly Ala Val Gly Val Met Phe His Ala Val Pro Gly Lys Glu Gly Asp
                660                 665                 670

Leu Trp Leu Ala Ala Ser Ser Gly Leu Tyr His Ser Thr Asn Gly Gly
                675                 680                 685

Ser Ser Trp Ser Ala Ile Thr Gly Val Ser Ser Ala Val Asn Val Gly
690                 695                 700

Phe Gly Lys Ser Ala Pro Gly Ser Ser Tyr Pro Ala Val Phe Val Val
705                 710                 715                 720

Gly Thr Ile Gly Gly Val Thr Gly Ala Tyr Arg Ser Asp Asp Cys Gly
                725                 730                 735

Thr Thr Trp Val Leu Ile Asn Asp Asp Gln His Gln Tyr Gly Asn Trp
                740                 745                 750

Gly Gln Ala Ile Thr Gly Asp His Ala Asn Leu Arg Arg Val Tyr Ile
            755                 760                 765

Gly Thr Asn Gly Arg Gly Ile Val Tyr Gly Asp Ile Gly Gly Ala Pro
        770                 775                 780

Ser Gly Ser Pro Ser Pro Ser Val Ser Pro Ser Ala Ser Pro Ser Leu
785                 790                 795                 800

Ser Pro Ser Pro Ser Pro Ser Ser Pro Ser Pro Ser Pro Ser Pro
                805                 810                 815

Ser Ser Ser Pro Ser Ser Ser Pro Ser Pro Ser Pro Ser Pro Ser Pro
                820                 825                 830

Ser Pro Ser Arg Ser Pro Ser Pro Ser Ala Ser Pro Ser Pro Ser Ser
            835                 840                 845

Ser Pro Ser Pro Ser Ser Ser Pro Ser Ser Ser Pro Ser Pro Thr Pro
        850                 855                 860

Ser Ser Ser Pro Val Ser Gly Gly Val Lys Val Gln Tyr Lys Asn Asn
865                 870                 875                 880

Asp Ser Ala Pro Gly Asp Asn Gln Ile Lys Pro Gly Leu Gln Val Val
                885                 890                 895

Asn Thr Gly Ser Ser Ser Val Asp Leu Ser Thr Val Thr Val Arg Tyr
                900                 905                 910

Trp Phe Thr Arg Asp Gly Gly Ser Ser Thr Leu Val Tyr Asn Cys Asp
            915                 920                 925

Trp Ala Ala Ile Gly Cys Gly Asn Ile Arg Ala Ser Phe Gly Ser Val
        930                 935                 940

Asn Pro Ala Thr Pro Thr Ala Asp Thr Tyr Leu Gln Xaa
945                 950                 955
```

<210> SEQ ID NO 2
<211> LENGTH: 2869
<212> TYPE: DNA
<213> ORGANISM: Acidothermus cellulolyticus
<220> FEATURE:
<221> NAME/KEY: misc_feature
<222> LOCATION: (2869)..(2869)
<223> OTHER INFORMATION: n is a, c, g, or t

<400> SEQUENCE: 2

| | | | | | |
|---|---|---|---|---|---|
| atggatcgtt | cggagaacat | ccgtctgact | atgagatcac | gacgattggt | atcactgctc    60 |
| gccgccactg | cgtcgttcgc | cgtggccgcc | gctctgggag | ttctgcccat | cgcgataacg   120 |
| gcttctcctg | cgcacgcggc | gacgactcag | ccgtacacct | ggagcaacgt | ggcgatcggg   180 |
| ggcggcggct | ttgtcgacgg | gatcgtcttc | aatgaaggtg | caccgggaat | tctgtacgtg   240 |
| cggacggaca | tcgggggggat | gtatcgatgg | gatgccgcca | acgggcggtg | gatccctctt   300 |
| ctggattggg | tgggatggaa | caattggggg | tacaacggcg | tcgtcagcat | tgcggcagac   360 |
| ccgatcaata | ctaacaaggt | atgggccgcc | gtcggaatgt | acaccaacag | ctgggaccca   420 |
| aacgacggag | cgattctccg | ctcgtctgat | cagggcgcaa | cgtggcaaat | aacgcccctg   480 |
| ccgttcaagc | ttggcggcaa | catgcccggg | cgtggaatgg | gcgagcggct | tgcggtggat   540 |
| ccaaacaatg | acaacattct | gtatttcggc | gccccgagcg | gcaaagggct | ctggagaagc   600 |
| acagattccg | gcgcgacctg | gtcccagatg | acgaactttc | cggacgtagg | cacgtacatt   660 |
| gcaaatccca | ctgacacgac | cggctatcag | agcgatattc | aaggcgtcgt | ctgggtcgct   720 |
| ttcgacaagt | cttcgtcatc | gctcgggcaa | gcgagtaaga | ccatttttgt | gggcgtggcg   780 |
| gatcccaata | atccggtctt | ctggagcaga | gacggcggcg | cgacgtggca | ggcggtgccg   840 |
| ggtgcgccga | ccggcttcat | cccgcacaag | ggcgtctttg | acccggtcaa | ccacgtgctc   900 |
| tatattgcca | ccagcaatac | gggtggtccg | tatgacggga | gctccggcga | cgtctggaaa   960 |
| ttctcggtga | cctccgggac | atggacgcga | atcagcccgg | taccttcgac | ggacacggcc  1020 |
| aacgactact | ttggttacag | cggcctcact | atcgaccgcc | agcacccgaa | cacgataatg  1080 |
| gtggcaaccc | agatatcgtg | gtggccggac | accataatct | tcggagcac | cgacggcggt  1140 |
| gcgacgtgga | cgcggatctg | ggattggacg | agttatccca | atcgaagctt | gcgatatgtg  1200 |
| cttgacattt | cggcggagcc | ttggctgacc | ttcggcgtac | agccgaatcc | tcccgtaccc  1260 |
| agtccgaagc | tcggctggat | ggatgaagcg | atggcaatcg | atccgttcaa | ctctgatcgg  1320 |
| atgctctacg | gaacaggcgc | gacgttgtac | gcaacaaatg | atctcacgaa | gtgggactcc  1380 |
| ggcggccaga | ttcatatcgc | gccgatggtc | aaaggattgg | aggagacggc | ggtaaacgat  1440 |
| ctcatcagcc | cgccgtctgg | cgccccgctc | atcagcgctc | tcggagacct | cggcggcttc  1500 |
| acccacgccg | acgttactgc | cgtgccatcg | acgatcttca | cgtcaccggt | gttcacgacc  1560 |
| ggcaccagcg | tcgactatgc | ggaattgaat | ccgtcgatca | tcgttcgcgc | tggaagtttc  1620 |
| gatccatcga | gccaaccgaa | cgacaggcac | gtcgcgttct | cgacagacgg | cggcaagaac  1680 |
| tggttccaag | gcagcgaacc | tggcggggtg | acgacgggcg | gcaccgtcgc | cgcatcggcc  1740 |
| gacggctctc | gtttcgtctg | ggctcccggc | gatcccggtc | agcctgtggt | gtacgcagtc  1800 |
| ggatttggca | actcctgggc | tgcttcgcaa | ggtgttcccg | ccaatgccca | gatccgctca  1860 |
| gaccgggtga | atccaaagac | tttctatgcc | ctatccaatg | gaaccttcta | tcgaagcacg  1920 |
| gacgcggccg | tgacattcca | accggtcgcg | gccggtcttc | cgagcagcgg | tgccgtcggt  1980 |
| gtcatgttcc | acgcggtgcc | tggaaaagaa | ggcgatctgt | ggctcgctgc | atcgagcggg  2040 |

```
ctttaccact caaccaatgg cggcagcagt tggtctgcaa tcaccggcgt atcctccgcg    2100
gtgaacgtgg gatttggtaa gtctgcgccc gggtcgtcat acccagccgt ctttgtcgtc    2160
ggcacgatcg gaggcgttac gggggcgtac cgctccgacg actgtgggac gacctgggta    2220
ctgatcaatg atgaccagca ccaatacgga aattgggggac aagcaatcac cggtgaccac    2280
gcgaatttac ggcgggtgta cataggcacg aacggccgtg gaattgtata cggggacatt    2340
ggtggtgcgc cgtccggatc gccgtctccg tcggtgagtc cgtcggcttc gccgagcctg    2400
agcccgagcc cgagcccgag cagctcgcca tcgccgtcgc cgtcgccgag ctcgagtcca    2460
tcctcgtcgc cgtctccgtc gccgtcacca tcgccgagtc cgtctcggtc tccgtcacca    2520
tcggcgtcgc cgagcccgtc ttcgtcaccg agcccgtctt cgtcaccgtc ttcgtcgccg    2580
agcccaacgc cgtcgtcgtc gccggtgtcg ggtggggtga aggtgcagta taagaataat    2640
gattcggcgc cgggtgataa tcagatcaag ccgggtttgc aggtggtgaa taccgggtcg    2700
tcgtcggtgg atttgtcgac ggtgacggtg cggtactggt tcacccggga tggtggctcg    2760
tcgacactgg tgtacaactg tgactgggcg gcgatcgggt gtgggaatat ccgcgcctcg    2820
ttcggctcgg tgaacccggc gacgccgacg gcggacacct acctgcagn              2869
```

<210> SEQ ID NO 3
<211> LENGTH: 740
<212> TYPE: PRT
<213> ORGANISM: Acidothermus cellulolyticus

<400> SEQUENCE: 3

```
Ala Thr Thr Gln Pro Tyr Thr Trp Ser Asn Val Ala Ile Gly Gly Gly
1               5                   10                  15

Gly Phe Val Asp Gly Ile Val Phe Asn Glu Gly Ala Pro Gly Ile Leu
            20                  25                  30

Tyr Val Arg Thr Asp Ile Gly Gly Met Tyr Arg Trp Asp Ala Ala Asn
        35                  40                  45

Gly Arg Trp Ile Pro Leu Leu Asp Trp Val Gly Trp Asn Asn Trp Gly
    50                  55                  60

Tyr Asn Gly Val Val Ser Ile Ala Ala Asp Pro Ile Asn Thr Asn Lys
65                  70                  75                  80

Val Trp Ala Ala Val Gly Met Tyr Thr Asn Ser Trp Asp Pro Asn Asp
                85                  90                  95

Gly Ala Ile Leu Arg Ser Ser Asp Gln Gly Ala Thr Trp Gln Ile Thr
            100                 105                 110

Pro Leu Pro Phe Lys Leu Gly Gly Asn Met Pro Gly Arg Gly Met Gly
        115                 120                 125

Glu Arg Leu Ala Val Asp Pro Asn Asn Asp Asn Ile Leu Tyr Phe Gly
    130                 135                 140

Ala Pro Ser Gly Lys Gly Leu Trp Arg Ser Thr Asp Ser Gly Ala Thr
145                 150                 155                 160

Trp Ser Gln Met Thr Asn Phe Pro Asp Val Gly Thr Tyr Ile Ala Asn
                165                 170                 175

Pro Thr Asp Thr Thr Gly Tyr Gln Ser Asp Ile Gln Gly Val Val Trp
            180                 185                 190

Val Ala Phe Asp Lys Ser Ser Ser Leu Gly Gln Ala Ser Lys Thr
        195                 200                 205

Ile Phe Val Gly Val Ala Asp Pro Asn Asn Pro Val Phe Trp Ser Arg
    210                 215                 220

Asp Gly Gly Ala Thr Trp Gln Ala Val Pro Gly Ala Pro Thr Gly Phe
225                 230                 235                 240
```

```
Ile Pro His Lys Gly Val Phe Asp Pro Val Asn His Val Leu Tyr Ile
            245                 250                 255

Ala Thr Ser Asn Thr Gly Gly Pro Tyr Asp Gly Ser Ser Gly Asp Val
            260                 265                 270

Trp Lys Phe Ser Val Thr Ser Gly Thr Trp Thr Arg Ile Ser Pro Val
            275                 280                 285

Pro Ser Thr Asp Thr Ala Asn Asp Tyr Phe Gly Tyr Ser Gly Leu Thr
            290                 295                 300

Ile Asp Arg Gln His Pro Asn Thr Ile Met Val Ala Thr Gln Ile Ser
305                 310                 315                 320

Trp Trp Pro Asp Thr Ile Ile Phe Arg Ser Thr Asp Gly Gly Ala Thr
            325                 330                 335

Trp Thr Arg Ile Trp Asp Trp Thr Ser Tyr Pro Asn Arg Ser Leu Arg
            340                 345                 350

Tyr Val Leu Asp Ile Ser Ala Glu Pro Trp Leu Thr Phe Gly Val Gln
            355                 360                 365

Pro Asn Pro Pro Val Pro Ser Pro Lys Leu Gly Trp Met Asp Glu Ala
            370                 375                 380

Met Ala Ile Asp Pro Phe Asn Ser Asp Arg Met Leu Tyr Gly Thr Gly
385                 390                 395                 400

Ala Thr Leu Tyr Ala Thr Asn Asp Leu Thr Lys Trp Asp Ser Gly Gly
            405                 410                 415

Gln Ile His Ile Ala Pro Met Val Lys Gly Leu Glu Glu Thr Ala Val
            420                 425                 430

Asn Asp Leu Ile Ser Pro Pro Ser Gly Ala Pro Leu Ile Ser Ala Leu
            435                 440                 445

Gly Asp Leu Gly Gly Phe Thr His Ala Asp Val Thr Ala Val Pro Ser
            450                 455                 460

Thr Ile Phe Thr Ser Pro Val Phe Thr Thr Gly Thr Ser Val Asp Tyr
465                 470                 475                 480

Ala Glu Leu Asn Pro Ser Ile Ile Val Arg Ala Gly Ser Phe Asp Pro
            485                 490                 495

Ser Ser Gln Pro Asn Asp Arg His Val Ala Phe Ser Thr Asp Gly Gly
            500                 505                 510

Lys Asn Trp Phe Gln Gly Ser Glu Pro Gly Gly Val Thr Thr Gly Gly
            515                 520                 525

Thr Val Ala Ala Ser Ala Asp Gly Ser Arg Phe Val Trp Ala Pro Gly
            530                 535                 540

Asp Pro Gly Gln Pro Val Val Tyr Ala Val Gly Phe Gly Asn Ser Trp
545                 550                 555                 560

Ala Ala Ser Gln Gly Val Pro Ala Asn Ala Gln Ile Arg Ser Asp Arg
            565                 570                 575

Val Asn Pro Lys Thr Phe Tyr Ala Leu Ser Asn Gly Thr Phe Tyr Arg
            580                 585                 590

Ser Thr Asp Gly Gly Val Thr Phe Gln Pro Val Ala Ala Gly Leu Pro
            595                 600                 605

Ser Ser Gly Ala Val Gly Val Met Phe His Ala Val Pro Gly Lys Glu
            610                 615                 620

Gly Asp Leu Trp Leu Ala Ala Ser Ser Gly Leu Tyr His Ser Thr Asn
625                 630                 635                 640

Gly Gly Ser Ser Trp Ser Ala Ile Thr Gly Val Ser Ser Ala Val Asn
            645                 650                 655

Val Gly Phe Gly Lys Ser Ala Pro Gly Ser Ser Tyr Pro Ala Val Phe
```

```
                    660                 665                 670
Val Val Gly Thr Ile Gly Gly Val Thr Gly Ala Tyr Arg Ser Asp Asp
            675                 680                 685

Cys Gly Thr Thr Trp Val Leu Ile Asn Asp Asp Gln His Gln Tyr Gly
            690                 695                 700

Asn Trp Gly Gln Ala Ile Thr Gly Asp His Ala Asn Leu Arg Arg Val
705                 710                 715                 720

Tyr Ile Gly Thr Asn Gly Arg Gly Ile Val Tyr Gly Asp Ile Gly Gly
            725                 730                 735

Ala Pro Ser Gly
            740

<210> SEQ ID NO 4
<211> LENGTH: 89
<212> TYPE: PRT
<213> ORGANISM: Acidothermus cellulolyticus
<220> FEATURE:
<221> NAME/KEY: misc_feature
<222> LOCATION: (89)..(89)
<223> OTHER INFORMATION: Xaa can be any naturally occurring amino acid

<400> SEQUENCE: 4

Val Ser Gly Gly Val Lys Val Gln Tyr Lys Asn Asn Asp Ser Ala Pro
1               5                  10                  15

Gly Asp Asn Gln Ile Lys Pro Gly Leu Gln Leu Val Asn Thr Gly Ser
                20                  25                  30

Ser Ser Val Asp Leu Ser Thr Val Thr Val Arg Tyr Trp Phe Thr Arg
            35                  40                  45

Asp Gly Gly Ser Ser Thr Leu Val Tyr Asn Cys Asp Trp Ala Ala Met
        50                  55                  60

Gly Cys Gly Asn Ile Arg Ala Ser Phe Gly Ser Val Asn Pro Ala Thr
65                  70                  75                  80

Pro Thr Ala Asp Thr Tyr Leu Gln Xaa
                85

<210> SEQ ID NO 5
<211> LENGTH: 88
<212> TYPE: PRT
<213> ORGANISM: Acidothermus cellulolyticus

<400> SEQUENCE: 5

Val Ser Gly Gly Val Lys Val Gln Tyr Lys Asn Asn Asp Ser Ala Pro
1               5                  10                  15

Gly Asp Asn Gln Ile Lys Pro Gly Leu Gln Leu Val Asn Thr Gly Ser
                20                  25                  30

Ser Ser Val Asp Leu Ser Thr Val Thr Val Arg Tyr Trp Phe Thr Arg
            35                  40                  45

Asp Gly Gly Ser Ser Thr Leu Val Tyr Asn Cys Asp Trp Ala Ala Met
        50                  55                  60

Gly Cys Gly Asn Ile Arg Ala Ser Phe Gly Ser Val Asn Pro Ala Thr
65                  70                  75                  80

Pro Thr Ala Asp Thr Tyr Leu Gln
                85

<210> SEQ ID NO 6
<211> LENGTH: 740
<212> TYPE: PRT
<213> ORGANISM: Acidothermus cellulolyticus

<400> SEQUENCE: 6
```

```
Ala Thr Thr Gln Pro Tyr Thr Trp Ser Asn Val Ala Ile Gly Gly
  1               5                  10                  15

Gly Phe Val Asp Gly Ile Val Phe Asn Glu Gly Ala Pro Gly Ile Leu
         20                  25                  30

Tyr Val Arg Thr Asp Ile Gly Gly Met Tyr Arg Trp Ala Ala Asn
         35                  40                  45

Gly Arg Trp Ile Pro Leu Leu Asp Trp Val Gly Trp Asn Asn Trp Gly
 50                  55                  60

Tyr Asn Gly Val Val Ser Ile Ala Ala Asp Pro Ile Asn Thr Asn Lys
 65                  70                  75                  80

Val Trp Ala Ala Val Gly Met Tyr Thr Asn Ser Trp Asp Pro Asn Asp
             85                  90                  95

Gly Ala Ile Leu Arg Ser Ser Asp Gln Gly Ala Thr Trp Gln Ile Thr
                100                 105                 110

Pro Leu Pro Phe Lys Leu Gly Gly Asn Met Pro Gly Arg Gly Met Gly
                115                 120                 125

Glu Arg Leu Ala Val Asp Pro Asn Asn Asp Asn Ile Leu Tyr Phe Gly
            130                 135                 140

Ala Pro Ser Gly Lys Gly Leu Trp Arg Ser Thr Asp Ser Gly Ala Thr
145                 150                 155                 160

Trp Ser Gln Met Thr Asn Phe Pro Asp Val Gly Thr Tyr Ile Ala Asn
                165                 170                 175

Pro Thr Asp Thr Thr Gly Tyr Gln Ser Asp Ile Gln Gly Val Val Trp
            180                 185                 190

Val Ala Phe Asp Lys Ser Ser Ser Leu Gly Gln Ala Ser Lys Thr
            195                 200                 205

Ile Phe Val Gly Val Ala Asp Pro Asn Pro Val Phe Trp Ser Arg
    210                 215                 220

Asp Gly Gly Ala Thr Trp Gln Ala Val Pro Gly Ala Pro Thr Gly Phe
225                 230                 235                 240

Ile Pro His Lys Gly Val Phe Asp Pro Val Asn His Val Leu Tyr Ile
                245                 250                 255

Ala Thr Ser Asn Thr Gly Gly Pro Tyr Asp Gly Ser Ser Gly Asp Val
                260                 265                 270

Trp Lys Phe Ser Val Thr Ser Gly Thr Trp Thr Arg Ile Ser Pro Val
            275                 280                 285

Pro Ser Thr Asp Thr Ala Asn Asp Tyr Phe Gly Tyr Ser Gly Leu Thr
    290                 295                 300

Ile Asp Arg Gln His Pro Asn Thr Ile Met Val Ala Thr Gln Ile Ser
305                 310                 315                 320

Trp Trp Pro Asp Thr Ile Ile Phe Arg Ser Thr Asp Gly Gly Ala Thr
                325                 330                 335

Trp Thr Arg Ile Trp Asp Trp Thr Ser Tyr Pro Asn Arg Ser Leu Arg
            340                 345                 350

Tyr Val Leu Asp Ile Ser Ala Glu Pro Trp Leu Thr Phe Gly Val Gln
    355                 360                 365

Pro Asn Pro Pro Val Pro Ser Pro Lys Leu Gly Trp Met Asp Glu Ala
    370                 375                 380

Met Ala Ile Asp Pro Phe Asn Ser Asp Arg Met Leu Tyr Gly Thr Gly
385                 390                 395                 400

Ala Thr Leu Tyr Ala Thr Asn Asp Leu Thr Lys Trp Asp Ser Gly Gly
            405                 410                 415

Gln Ile His Ile Ala Pro Met Val Lys Gly Leu Glu Glu Thr Ala Val
```

```
                420                 425                 430
Asn Asp Leu Ile Ser Pro Pro Ser Gly Ala Pro Leu Ile Ser Ala Leu
            435                 440                 445

Gly Asp Leu Gly Gly Phe Thr His Ala Asp Val Thr Ala Val Pro Ser
        450                 455                 460

Thr Ile Phe Thr Ser Pro Val Phe Thr Thr Gly Thr Ser Val Asp Tyr
465                 470                 475                 480

Ala Glu Leu Asn Pro Ser Ile Ile Val Arg Ala Gly Ser Phe Asp Pro
                485                 490                 495

Ser Ser Gln Pro Asn Asp Arg His Val Ala Phe Ser Thr Asp Gly Gly
            500                 505                 510

Lys Asn Trp Phe Gln Gly Ser Glu Pro Gly Gly Val Thr Thr Gly Gly
        515                 520                 525

Thr Val Ala Ala Ser Ala Asp Gly Ser Arg Phe Val Trp Ala Pro Gly
    530                 535                 540

Asp Pro Gly Gln Pro Val Val Tyr Ala Val Gly Phe Gly Asn Ser Trp
545                 550                 555                 560

Ala Ala Ser Gln Gly Val Pro Ala Asn Ala Gln Ile Arg Ser Asp Arg
                565                 570                 575

Val Asn Pro Lys Thr Phe Tyr Ala Leu Ser Asn Gly Thr Phe Tyr Arg
            580                 585                 590

Ser Thr Asp Gly Gly Val Thr Phe Gln Pro Val Ala Ala Gly Leu Pro
        595                 600                 605

Ser Ser Gly Ala Val Gly Val Met Phe His Ala Val Pro Gly Lys Glu
    610                 615                 620

Gly Asp Leu Trp Leu Ala Ala Ser Ser Gly Leu Tyr His Ser Thr Asn
625                 630                 635                 640

Gly Gly Ser Ser Trp Ser Ala Ile Thr Gly Val Ser Ser Ala Val Asn
                645                 650                 655

Val Gly Phe Gly Lys Ser Ala Pro Gly Ser Ser Tyr Pro Ala Val Phe
            660                 665                 670

Val Val Gly Thr Ile Gly Gly Val Thr Gly Ala Tyr Arg Ser Asp Asp
        675                 680                 685

Cys Gly Thr Thr Trp Val Leu Ile Asn Asp Asp Gln His Gln Tyr Gly
    690                 695                 700

Asn Trp Gly Gln Ala Ile Thr Gly Asp His Ala Asn Leu Arg Arg Val
705                 710                 715                 720

Tyr Ile Gly Thr Asn Gly Arg Gly Ile Val Tyr Gly Asp Ile Gly Gly
                725                 730                 735

Ala Pro Ser Gly
            740

<210> SEQ ID NO 7
<211> LENGTH: 726
<212> TYPE: PRT
<213> ORGANISM: Aspergillus aculeatus

<400> SEQUENCE: 7

Ala Ala Ser Gln Ala Tyr Thr Trp Lys Asn Val Val Thr Gly Gly Gly
1               5                   10                  15

Gly Gly Phe Thr Pro Gly Ile Val Phe Asn Pro Ser Ala Lys Gly Val
            20                  25                  30

Ala Tyr Ala Arg Thr Asp Ile Gly Gly Ala Tyr Arg Leu Asn Ser Asp
        35                  40                  45

Asp Thr Trp Thr Pro Leu Met Asp Trp Val Gly Asn Asp Thr Trp His
```

```
            50                  55                  60
Asp Trp Gly Ile Asp Ala Leu Ala Thr Asp Pro Val Asp Thr Asp Arg
 65                  70                  75                  80

Val Tyr Val Ala Val Gly Met Tyr Thr Asn Glu Trp Asp Pro Asn Val
                 85                  90                  95

Gly Ser Ile Leu Arg Ser Thr Asp Gln Gly Asp Thr Trp Thr Glu Thr
                100                 105                 110

Lys Leu Pro Phe Lys Val Gly Gly Asn Met Pro Gly Arg Gly Met Gly
                115                 120                 125

Glu Arg Leu Ala Val Asp Pro Asn Lys Asn Ser Ile Leu Tyr Phe Gly
130                 135                 140

Ala Arg Ser Gly His Gly Leu Trp Lys Ser Thr Asp Tyr Gly Ala Thr
145                 150                 155                 160

Trp Ser Asn Val Thr Ser Phe Thr Trp Thr Gly Thr Tyr Phe Gln Asp
                165                 170                 175

Ser Ser Ser Thr Tyr Thr Ser Asp Pro Val Gly Ile Ala Trp Val Thr
                180                 185                 190

Phe Asp Ser Thr Ser Gly Ser Ser Gly Ser Ala Thr Pro Arg Ile Phe
                195                 200                 205

Val Gly Val Ala Asp Ala Gly Lys Ser Val Phe Lys Ser Glu Asp Ala
210                 215                 220

Gly Ala Thr Trp Ala Trp Val Ser Gly Glu Pro Gln Tyr Gly Phe Leu
225                 230                 235                 240

Pro His Lys Gly Val Leu Ser Pro Glu Glu Lys Thr Leu Tyr Ile Ser
                245                 250                 255

Tyr Ala Asn Gly Ala Gly Pro Tyr Asp Gly Thr Asn Gly Thr Val His
                260                 265                 270

Lys Tyr Asn Ile Thr Ser Gly Val Trp Thr Asp Ile Ser Pro Thr Ser
                275                 280                 285

Leu Ala Ser Thr Tyr Tyr Gly Tyr Gly Gly Leu Ser Val Asp Leu Gln
                290                 295                 300

Val Pro Gly Thr Leu Met Val Ala Ala Leu Asn Cys Trp Trp Pro Asp
305                 310                 315                 320

Glu Leu Ile Phe Arg Ser Thr Asp Ser Gly Ala Thr Trp Ser Pro Ile
                325                 330                 335

Trp Glu Trp Asn Gly Tyr Pro Ser Ile Asn Tyr Tyr Ser Tyr Asp
                340                 345                 350

Ile Ser Asn Ala Pro Trp Ile Gln Asp Thr Thr Ser Thr Asp Gln Phe
                355                 360                 365

Pro Val Arg Val Gly Trp Met Val Glu Ala Leu Ala Ile Asp Pro Phe
370                 375                 380

Asp Ser Asn His Trp Leu Tyr Gly Thr Gly Leu Thr Val Tyr Gly Gly
385                 390                 395                 400

His Asp Leu Thr Asn Trp Asp Ser Lys His Asn Val Thr Val Lys Ser
                405                 410                 415

Leu Ala Val Gly Ile Glu Glu Met Ala Val Leu Gly Leu Ile Thr Pro
                420                 425                 430

Pro Gly Gly Pro Ala Leu Leu Ser Ala Val Gly Asp Asp Gly Gly Phe
                435                 440                 445

Tyr His Ser Asp Leu Asp Ala Ala Pro Asn Gln Ala Tyr His Thr Pro
                450                 455                 460

Thr Tyr Gly Thr Thr Asn Gly Ile Asp Tyr Ala Gly Asn Lys Pro Ser
465                 470                 475                 480
```

```
Asn Ile Val Arg Ser Gly Ala Ser Asp Asp Tyr Pro Thr Leu Ala Leu
            485                 490                 495

Ser Ser Asn Phe Gly Ser Thr Trp Tyr Ala Asp Tyr Ala Ala Ser Thr
            500                 505                 510

Ser Thr Gly Thr Gly Ala Val Ala Leu Ser Ala Asp Gly Asp Thr Val
            515                 520                 525

Leu Leu Met Ser Ser Thr Ser Gly Ala Leu Val Ser Lys Ser Gln Gly
            530                 535                 540

Thr Leu Thr Ala Val Ser Ser Leu Pro Ser Gly Ala Val Ile Ala Ser
545                 550                 555                 560

Asp Lys Ser Asp Asn Thr Val Phe Tyr Gly Ser Ala Gly Ala Ile
            565                 570                 575

Tyr Val Ser Lys Asn Thr Ala Thr Ser Phe Thr Lys Thr Val Ser Leu
            580                 585                 590

Gly Ser Ser Thr Thr Val Asn Ala Ile Arg Ala His Pro Ser Ile Ala
            595                 600                 605

Gly Asp Val Trp Ala Ser Thr Asp Lys Gly Leu Trp His Ser Thr Asp
            610                 615                 620

Tyr Gly Ser Thr Phe Thr Gln Ile Gly Ser Gly Val Thr Ala Gly Trp
625                 630                 635                 640

Ser Phe Gly Phe Gly Lys Ala Ser Ser Thr Gly Ser Tyr Val Val Ile
            645                 650                 655

Tyr Gly Phe Phe Thr Ile Asp Gly Ala Ala Gly Leu Phe Lys Ser Glu
            660                 665                 670

Asp Ala Gly Thr Asn Trp Gln Val Ile Ser Asp Ala Ser His Gly Phe
            675                 680                 685

Gly Ser Gly Ser Ala Asn Val Val Asn Gly Asp Leu Gln Thr Tyr Gly
            690                 695                 700

Arg Val Phe Arg Gly His Glu Arg Pro Gly His Leu Leu Arg Gln Ser
705                 710                 715                 720

Gln Arg Glu Pro Ala Gly
            725

<210> SEQ ID NO 8
<211> LENGTH: 36
<212> TYPE: PRT
<213> ORGANISM: Acidothermus cellulolyticus

<400> SEQUENCE: 8

Met Arg Ser Arg Arg Leu Val Ser Leu Leu Ala Ala Thr Ala Ser Phe
1               5                   10                  15

Ala Val Ala Ala Ala Leu Gly Val Leu Pro Ile Ala Ile Thr Ala Ser
            20                  25                  30

Pro Ala His Ala
            35
```

METHODS OF USING THERMAL TOLERANT AVICELASE FROM *ACIDOTHERMUS CELLULOLYTICUS*

CROSS-REFERENCE TO RELATED APPLICATIONS

This application is a division of U.S. application Ser. No. 10/155,400, filed Oct. 18, 2002, now U.S. Pat. No. 7,538,200, issued May 26, 2009, which is a division of U.S. application Ser. No. 09/917,376, filed Jul. 28, 2001, now U.S. Pat. No. 7,364,890, issued Apr. 29, 2008. The contents of each application listed above are incorporated by reference in their entirety.

GOVERNMENT INTERESTS

The United States Government has rights in this invention under Contract No. DE-AC36-08GO28308 between the United States Department of Energy and the Alliance for Sustainable Energy, LLC, manager and operator of the National Renewable Energy Laboratory.

FIELD OF THE INVENTION

The invention generally relates to a novel avicelase from *Acidothermus cellulolyticus*, AviIII. More specifically, the invention relates to purified and isolated AviIII polypeptides, nucleic acid molecules encoding the polypeptides, and processes for production and use of AviIII, as well as variants and derivatives thereof.

BACKGROUND OF THE INVENTION

Plant biomass as a source of energy production can include agricultural and forestry products, associated by-products and waste, municipal solid waste, and industrial waste. In addition, over 50 million acres in the United States are currently available for biomass production, and there are a number of terrestrial and aquatic crops grown solely as a source for biomass (A Wiselogel, et al. Biomass feedstocks resources and composition—in C E Wyman, ed. Handbook on Bioethanol: Production and Utilization. Washington, D.C.: Taylor & Francis, 1996, pp 105-118). Biofuels produced from biomass include ethanol, methanol, biodiesel, and additives for reformulated gasoline. Biofuels are desirable because they add little, if any, net carbon dioxide to the atmosphere and because they greatly reduce ozone formation and carbon monoxide emissions as compared to the environmental output of conventional fuels. (P Bergeron. Environmental impacts of bioethanol—in C E Wyman, ed. Handbook on Bioethanol: Production and Utilization. Washington, D.C.: Taylor & Francis, 1996, pp 90-103).

Plant biomass is the most abundant source of carbohydrate in the world due to the lignocellulosic materials composing the cell walls of all higher plants. Plant cell walls are divided into two sections, the primary and the secondary cell walls. The primary cell wall, which provides structure for expanding cells (and hence changes as the cell grows), is composed of three major polysaccharides and one group of glycoproteins. The predominant polysaccharide, and most abundant source of carbohydrates, is cellulose, while hemicellulose and pectin are also found in abundance. Cellulose is a linear beta-(1,4)-D-glucan and comprises 20% to 30% of the primary cell wall by weight. The secondary cell wall, which is produced after the cell has completed growing, also contains polysaccharides and is strengthened through polymeric lignin covalently cross-linked to hemicellulose.

Carbohydrates, and cellulose in particular can be converted to sugars by well-known methods including acid and enzymatic hydrolysis. Enzymatic hydrolysis of cellulose requires the processing of biomass to reduce size and facilitate subsequent handling. Mild acid treatment is then used to hydrolyze part or all of the hemicellulose content of the feedstock. Finally, cellulose is converted to ethanol through the concerted action of cellulases and saccharolytic fermentation (simultaneous saccharification fermentation (SSF)). The SSF process, using the yeast *Saccharomyces cerevisiae* for example, is often incomplete, as it does not utilize the entire sugar content of the plant biomass, namely the hemicellulose fraction.

The cost of producing ethanol from biomass can be divided into three areas of expenditure: pretreatment costs, fermentation costs, and other costs. Pretreatment costs include biomass milling, pretreatment reagents, equipment maintenance, power and water, and waste neutralization and disposal. The fermentation costs can include enzymes, nutrient supplements, yeast, maintenance and scale-up, and waste disposal. Other costs include biomass purchase, transportation and storage, plant labor, plant utilities, ethanol distillation, and administration (which may include technology-use licenses). One of the major expenses incurred in SSF is the cost of the enzymes, as about one kilogram of cellulase is required to fully digest 50 kilograms of cellulose. Economical production of cellulase is also compounded by factors such as the relatively slow growth rates of cellulase-producing organisms, levels of cellulase expression, and the tendency of enzyme-dependent processes to partially or completely inactivate enzymes due to conditions such as elevated temperature, acidity, proteolytic degradation, and solvent degradation.

Enzymatic degradation of cellulose requires the coordinate action of at least three different types of cellulases. Such enzymes are given an Enzyme Commission (EC) designation according to the Nomenclature Committee of the International Union of Biochemistry and Molecular Biology (Eur. J. Biochem. 264: 607-609 and 610-650, 1999). Endo-beta-(1, 4)-glucanases (EC 3.2.1.4) cleave the cellulose strand randomly along its length, thus generating new chain ends. Exo-beta-(1,4)-glucanases (EC 3.2.1.91) are processive enzymes and cleave cellobiosyl units (beta-(1,4)-glucose dimers) from free ends of cellulose strands. Lastly, beta-D-glucosidases (cellobiases: EC 3.2.1.21) hydrolyze cellobiose to glucose. All three of these general activities are required for efficient and complete hydrolysis of a polymer such as cellulose to a subunit, such as the simple sugar, glucose.

Highly thermostable enzymes have been isolated from the cellulolytic thermophile *Acidothermus cellulolyticus* gen. nov., sp. nov., a bacterium originally isolated from decaying wood in an acidic, thermal pool at Yellowstone National Park, A. Mohagheghi et al., (1986) *Int. J. Systematic Bacteriology*, 36(3): 435-443. One cellulase enzyme produced by this organism, the endoglucanase E1, is known to display maximal activity at 75° C. to 83° C. M. P. Tucker et al. (1989), *Bio/Technology*, 7(8): 817-820. E1 endoglucanase has been described in U.S. Pat. No. 5,275,944. The *A. cellulolyticus* E1 endoglucanase is an active cellulase; in combination with the exocellulase CBH I from *Trichoderma reesei*, E1 gives a high level of saccharification and contributes to a degree of synergism. Baker J O et al. (1994), *Appl. Biochem. Biotechnol.*, 45/46: 245-256. The gene coding E1 catalytic and carbohydrate binding domains and linker peptide were described in U.S. Pat. No. 5,536,655. E1 has also been expressed as a stable, active enzyme from a wide variety of hosts, including *E. coli, Streptomyces lividans, Pichia pastoris*, cotton, tobacco, and *Arabidopsis* (Dai Z, Hooker B S, Anderson D B, Thomas S R. Transgenic Res. 2000 February; 9(1):43-54).

There is a need within the art to generate alternative cellulase enzymes capable of assisting in the commercial-scale processing of cellulose to sugar for use in biofuel production. Against this backdrop the present invention has been developed. The potential exists for the successful, commercial-scale expression of heterologous cellulase polypeptides, and in particular novel cellulase polypeptides with or without any one or more desirable properties such as thermal tolerance, and partial or complete resistance to extreme pH inactivation, proteolytic inactivation, solvent inactivation, chaotropic agent inactivation, oxidizing agent inactivation, and detergent inactivation. Such expression can occur in fungi, bacteria, and other hosts.

SUMMARY OF THE INVENTION

The present invention provides AviIII, a novel member of the glycoside hydrolase (GH) family of enzymes, and in particular a thermal tolerant glycoside hydrolase useful in the degradation of cellulose. AviIII polypeptides of the invention include those having an amino acid sequence shown in SEQ ID NO:1, as well as polypeptides having substantial amino acid sequence identity to the amino acid sequence of SEQ ID NO:1 and useful fragments thereof, including, a catalytic domain having significant sequence similarity to the GH74 family, a carbohydrate binding domain (type III). See FIG. 1.

The invention also provides a polynucleotide molecule encoding AviIII polypeptides and fragments of AviIII polypeptides, for example catalytic and carbohydrate binding domains. Polynucleotide molecules of the invention include those molecules having a nucleic acid sequence as shown in SEQ ID NO:2; those that hybridize to the nucleic acid sequence of SEQ ID NO:2 under high stringency conditions; and those having substantial nucleic acid identity with the nucleic acid sequence of SEQ ID NO:2.

The invention includes variants and derivatives of the AviIII polypeptides, including fusion proteins. For example, fusion proteins of the invention include AviIII polypeptide fused to a heterologous protein or peptide that confers a desired function. The heterologous protein or peptide can facilitate purification, oligomerization, stabilization, or secretion of the AviIII polypeptide, for example. As further examples, the heterologous polypeptide can provide enhanced activity, including catalytic or binding activity, for AviIII polypeptides, where the enhancement is either additive or synergistic. A fusion protein of an embodiment of the invention can be produced, for example, from an expression construct containing a polynucleotide molecule encoding AviIII polypeptide in frame with a polynucleotide molecule for the heterologous protein. Embodiments of the invention also comprise vectors, plasmids, expression systems, host cells, and the like, containing a AviIII polynucleotide molecule. Genetic engineering methods for the production of AviIII polypeptides of embodiments of the invention include expression of a polynucleotide molecule in cell free expression systems and in cellular hosts, according to known methods.

The invention further includes compositions containing a substantially purified AviIII polypeptide of the invention and a carrier. Such compositions are administered to a biomass containing cellulose for the reduction or degradation of the cellulose.

The invention also provides reagents, compositions, and methods that are useful for analysis of AviIII activity.

These and various other features as well as advantages which characterize the present invention will be apparent from a reading of the following detailed description and a review of the associated drawings.

The following Tables 1 and 2 includes sequences used in describing embodiments of the present invention. In Table 1, the abbreviations are as follows: CD, catalytic domain; CBD_III, carbohydrate binding domain type III. When used herein, N* indicates a string of unknown nucleic acid units, and X* indicates a string of unknown amino acid units, for example about 50 or more. Table 1 includes approximate start and stop information for segments, and Table 2 includes amino acid sequence data for segments.

TABLE 1

Nucleotide and polypeptide segments.

| AviIII Segment | base BEGIN | base END | Length, bp | aa BEGIN No. | aa | aa END No. | aa | Length, aa | SEQ ID No. (amino acid) | SEQ ID No. (nucleotide) |
|---|---|---|---|---|---|---|---|---|---|---|
| Total length | 1 | about 3000 | about 3 kb | 1 | M | about 1000 | X* | about 1000 | 1 | 2 |
| Signal (potential) | 31 | 138 | 108 | 11 | M | 46 | A | 36 | | |
| CD (GH74) | 139 | 2358 | 2220 | 47 | A | 786 | G | 740 | 3 | |
| CBD_III (partial) | 2607 | about 3000 | about 0.5 kb | 869 | V | about 1000 | X* | about 154 | 4 | |
| CBD_III (partial) | 2607 | 2838 | 264 | 869 | V | 956 | Q | 88 | 5 | |

TABLE 2

```
                Gene/polypeptide segments with amino acid sequences.

SEQ ID No.    SEQ ID No.    AviIII
(amino acid)  (nucleotide)  Segment         Segment Data
     1             2        Total length    SEQ ID NO: 1 (see Table 3); SEQ ID NO: 2 (see Table 4)

8                      Signal          MRSRRLVSLLAATASFAVAAALGVLPIAITASPAHA
                            (potential)
```

TABLE 2-continued

Gene/polypeptide segments with amino acid sequences.

| SEQ ID No. (amino acid) | SEQ ID No. (nucleotide) | AviIII Segment | Segment Data |
|---|---|---|---|
| 1 | 2 | Total length | SEQ ID NO: 1 (see Table 3); SEQ ID NO: 2 (see Table 4) |
| 3 | | CD (GH74) | ATTQPYTWSNVAIGGGGFVDGIVFNEGAPGILYVRTDIGGMYRWDAANGRWIPLLDWVGWNNW GYNGVVSIAADPINTNKVWAAVGMYTNSWDPNDGAILRSSDQGATWQITPLPFKLGGNMPGRG MGERLAVDPNNDNILYFGAPSGKGLWRSTDSGATWSQMTNFPDVGTYIANPTOTTGYQSDIQG VVWVAFDKSSSSLGQASKTIFVGVAPPNNPVFWSRDGGATWQAVPGAPTGFIFHKGVFDFVNH VLYIATSNTGGPYDGSSGDVWKFSVTSGTWTRISPVPSTDTANDYFGYSGLTIDRQHFNTIMV ATQISWWPDTIIFRSTDGGATWTRIWDWTSYPNRSLRYVLD1SAEPWLTFGVQPNPPVPSPKL GWMDEAMAIDPFNSDRMLYGTGATLYATNDLTKWDSGGQIHIAPMVKGLEETAVNDLISPPSG APLISALGDLGGFTHADVTAVPSTIFTSPVFTTGTSVDYAELNPSIIVRAGSFDPSSQPNDRH VAFSTDGGKNWFQGSEPGGVTTGGTVAASADGSRFVWAPGDPGQPVVYAVGFGNSWAASQGVP ANAQIRSDRVNFKTFYALSNGTFYRSTDGGVTFQPVAAGLPSSGAVGVMFHAVPGKEGDLWLA ASSGLYHSTNGGSSWSAITGVSSAVNVGFGKSAPCSSYPAVFVVGTIGGVTGAYRSDDCGTTW VLINDDQHQTGNWGQAITGDHANLRRVYIGTNGRGIVYGDIGGAPSG |
| 4 | | COD_IlI (partial) | VSGGVKVQYKNNDSAPGDNQIKPGLQVVNTGSSSVDLSTVTVRYWFTRDGGSSTLVYNCDWAA IGCGNIRASFGSVNPATPTADTYLQX* |
| 5 | | COD_III (partial) | VSGGVKVQYKNNDSAPGDNQIKFGLQVVNTGSSSVDLSTVTVRYWFTRDGGSSTLVYNCDWAA IGCGNIRASFGSVNPATPTADTYLQ |

DETAILED DESCRIPTION

Definitions

Figure 1:
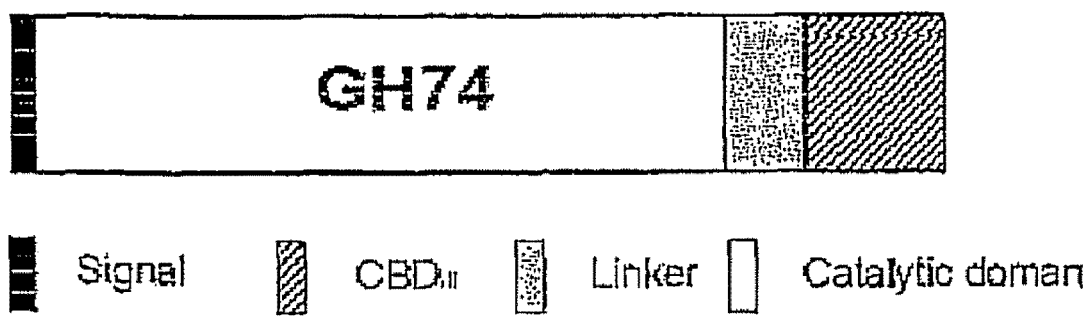
FIG. 1 is a schematic representation of the gene sequence and amino acid segment organization.
Figure 2:
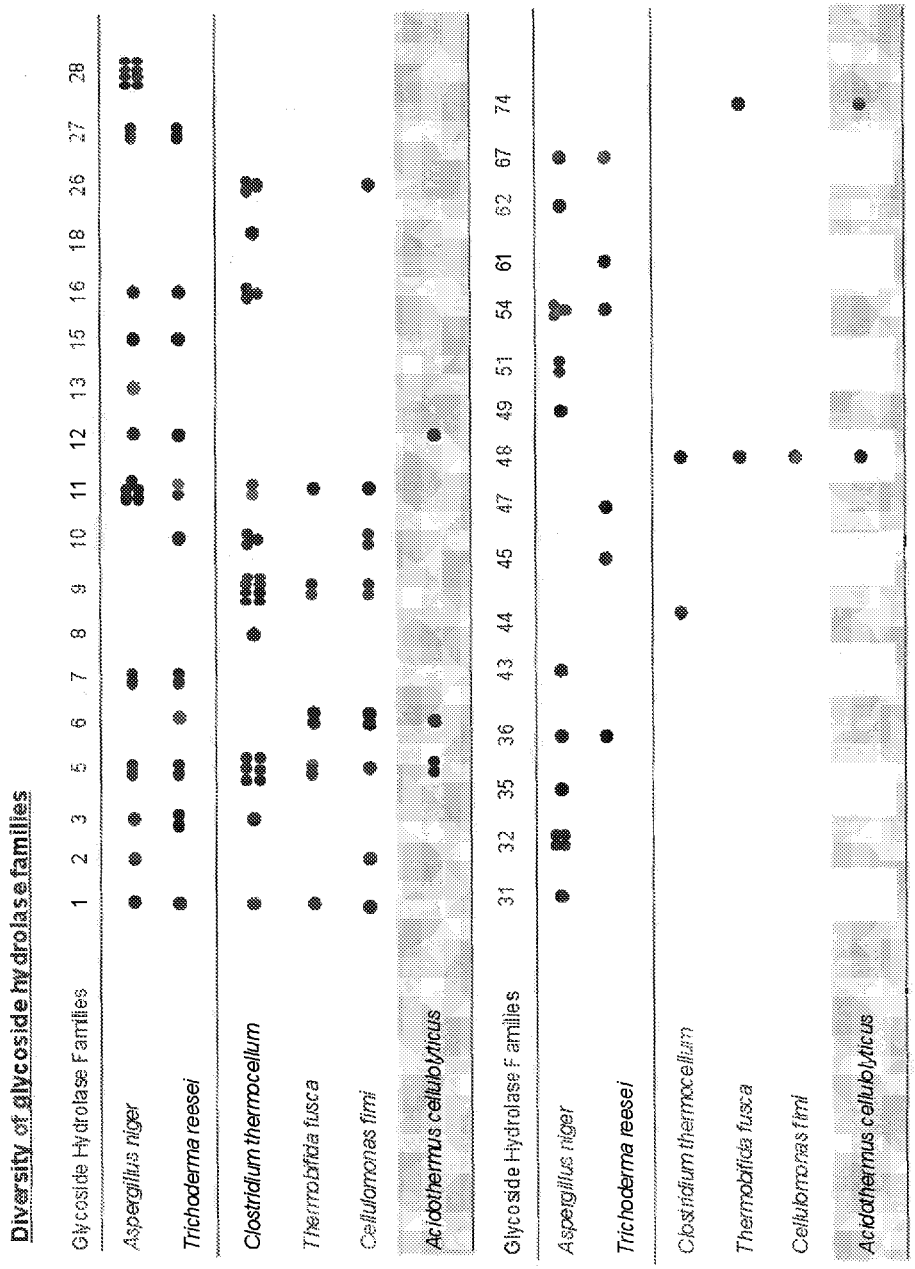
FIG. 2 is a graphic representation of the glycoside hydrolase gene/protein families found in various organisms. Each mark represents a single enzyme in the indicated glycoside hydrolase family (based on sequence homologies) that each listed organism contains.

The following definitions are provided to facilitate understanding of certain terms used frequently to herein and are not meant to limit the scope of the present disclosure:

"Amino acid" refers to any of the twenty naturally occurring amino acids as well as any modified amino acid sequences. Modifications may include natural processes such as posttranslational processing, or may include chemical modifications which are known in the art. Modifications include but are not limited to: phosphorylation, ubiquitination, acetylation, amidation, glycosylation, covalent attachment of flavin, ADP-ribosylation, cross linking, iodination, methylation, and alike.

"Antibody" refers to a Y-shaped molecule having a pair of antigen binding sites, a hinge region and a constant region. Fragments of antibodies, for example an antigen binding fragment (Fab), chimeric antibodies, antibodies having a human constant region coupled to a murine antigen binding region, and fragments thereof, as well as other well known recombinant antibodies are included in the present invention.

"Antisense" refers to polynucleotide sequences that are complementary to target "sense" polynucleotide sequence.

"Binding activity" refers to any activity that can be assayed by characterizing the ability of a polypeptide to bind to a substrate. The substrate can be a polymer such as cellulose or can be a complex molecule or aggregate of molecules where the entire moiety comprises at least some cellulose.

"Cellulase activity" refers to any activity that can be assayed by characterizing the enzymatic activity of a cellulase. For example, cellulase activity can be assayed by determining how much reducing sugar is produced during a fixed amount of time for a set amount of enzyme (see Irwin et al., (1998) *J. Bacteriology*, 1709-1714). Other assays are well known in the art and can be substituted.

"Complementary" or "complementarity" refers to the ability of a polynucleotide in a polynucleotide molecule to form a base pair with another polynucleotide in a second polynucleotide molecule. For example, the sequence A-G-T is complementary to the sequence T-C-A. Complementarity may be partial, in which only some of the polynucleotides match according to base pairing, or complete, where all the polynucleotides match according to base pairing.

"Expression" refers to transcription and translation occurring within a host cell. The level of expression of a DNA molecule in a host cell may be determined on the basis of either the amount of corresponding mRNA that is present within the cell or the amount of DNA molecule encoded protein produced by the host cell (Sambrook et al., 1989, *Molecular cloning: A Laboratory Manual*, 18.1-18.88).

"Fusion protein" refers to a first protein having attached a second, heterologous protein. Preferably, the heterologous protein is fused via recombinant DNA techniques, such that the first and second proteins are expressed in frame. The heterologous protein can confer a desired characteristic to the fusion protein, for example, a detection signal, enhanced stability or stabilization of the protein, facilitated oligomerization of the protein, or facilitated purification of the fusion protein. Examples of heterologous proteins useful in the fusion proteins of the invention include molecules having one or more catalytic domains of AviIII, one or more binding domains of AviIII, one or more catalytic domains of a glycoside hydrolase other than AviIII, one or more binding domains of a glycoside hydrolase other than AviIII, or any combination thereof. Further examples include immunoglobulin molecules and portions thereof, peptide tags such as histidine tag (6-His), leucine zipper, substrate targeting moieties, signal peptides, and the like. Fusion proteins are also meant to encompass variants and derivatives of AviIII polypeptides that are generated by conventional site-directed mutagenesis and more modern techniques such as directed evolution, discussed infra.

"Genetically engineered" refers to any recombinant DNA or RNA method used to create a prokaryotic or eukaryotic host cell that expresses a protein at elevated levels, at lowered levels, or in a mutated form. In other words, the host cell has been transfected, transformed, or transduced with a recombinant polynucleotide molecule, and thereby been altered so as to cause the cell to alter expression of the desired protein. Methods and vectors for genetically engineering host cells are well known in the art; for example various techniques are illustrated in Current Protocols in Molecular Biology, Ausubel et al., eds. (Wiley & Sons, New York, 1988, and quarterly updates). Genetically engineering techniques include but are not limited to expression vectors, targeted homologous recombination and gene activation (see, for example, U.S. Pat. No. 5,272,071 to Chappel) and trans activation by engineered transcription factors (see, for example, Segal et al., 1999, *Proc Natl Acad Sci USA* 96(6):2758-63).

"Glycoside hydrolase family" refers to a family of enzymes which hydrolyze the glycosidic bond between two or more carbohydrates or between a carbohydrate and a non-carbohydrate moiety (Henrissat B., (1991) Biochem. J., 280: 309-316). Identification of a putative glycoside hydrolase family member is made based on an amino acid sequence comparison and the finding of significant sequence similarity within the putative member's catalytic domain, as compared to the catalytic domains of known family members.

"Homology" refers to a degree of complementarity between polynucleotides, having significant effect on the efficiency and strength of hybridization between polynucleotide molecules. The term also can refer to a degree of similarity between polypeptides.

"Host cell" or "host cells" refers to cells expressing a heterologous polynucleotide molecule. Host cells of the present invention express polynucleotides encoding AviIII or a fragment thereof. Examples of suitable host cells useful in the present invention include, but are not limited to, prokaryotic and eukaryotic cells. Specific examples of such cells include bacteria of the genera *Escherichia*, *Bacillus*, and *Salmonella*, as well as members of the genera *Pseudomonas*, *Streptomyces*, and *Staphylococcus*; fungi, particularly filamentous fungi such as *Trichoderma* and *Aspergillus*, *Phanerochaete chrysosporium* and other white rot fungi; also other fungi including *Fusaria*, molds, and yeast including *Saccharomyces* sp., *Pichia* sp., and *Candida* sp. and the like; plants e.g. *Arabidopsis*, cotton, barley, tobacco, potato, and aquatic plants and the like; SF9 insect cells (Summers and Smith, 1987, *Texas Agriculture Experiment Station Bulletin*, 1555); and the like. Other specific examples include mammalian cells such as human embryonic kidney cells (293 cells), Chinese hamster ovary (CHO) cells (Puck et al., 1958, *Proc. Natl. Acad. Sci. USA* 60, 1275-1281), human cervical carcinoma cells (HELA) (ATCC CCL 2), human liver cells (Hep G2) (ATCC HB8065), human breast cancer cells (MCF-7) (ATCC HTB22), human colon carcinoma cells (DLD-1) (ATCC CCL 221), Daudi cells (ATCC CRL-213), murine myeloma cells such as P3/NSI/1-Ag4-1 (ATCC TIB-18), P3X63Ag8 (ATCC TIB-9), SP2/0-Ag14 (ATCC CRL-1581) and the like.

"Hybridization" refers to the pairing of complementary polynucleotides during an annealing period. The strength of hybridization between two polynucleotide molecules is impacted by the homology between the two molecules, stringency of the conditions involved, the melting temperature of the formed hybrid and the G:C ratio within the polynucleotides.

"Identity" refers to a comparison between pairs of nucleic acid or amino acid molecules. Methods for determining sequence identity are known. See, for example, computer programs commonly employed for this purpose, such as the Gap program (Wisconsin Sequence Analysis Package, Version 8 for Unix, Genetics Computer Group, University Research Park, Madison Wis.), that uses the algorithm of Smith and Waterman, 1981, *Adv. Appl. Math.*, 2: 482-489.

"Isolated" refers to a polynucleotide or polypeptide that has been separated from at least one contaminant (polynucleotide or polypeptide) with which it is normally associated. For example, an isolated polynucleotide or polypeptide is in a context or in a form that is different from that in which it is found in nature.

"Nucleic acid sequence" refers to the order or sequence of deoxyribonucleotides along a strand of deoxyribonucleic acid. The order of these deoxyribonucleotides determines the order of amino acids along a polypeptide chain. The deoxyribonucleotide sequence thus codes for the amino acid sequence.

"Polynucleotide" refers to a linear sequence of nucleotides. The nucleotides may be ribonucleotides, or deoxyribonucleotides, or a mixture of both. Examples of polynucleotides in the context of the present invention include single and double stranded DNA, single and double stranded RNA, and hybrid molecules having mixtures of single and double stranded DNA and RNA. The polynucleotides of the present invention may contain one or more modified nucleotides.

"Protein," "peptide," and "polypeptide" are used interchangeably to denote an amino acid polymer or a set of two or more interacting or bound amino acid polymers.

"Purify," or "purified" refers to a target protein that is free from at least 5-10% of contaminating proteins. Purification of a protein from contaminating proteins can be accomplished using known techniques, including ammonium sulfate or ethanol precipitation, acid precipitation, heat precipitation, anion or cation exchange chromatography, phosphocellulose chromatography, hydrophobic interaction chromatography, affinity chromatography, hydroxylapatite chromatography, size-exclusion chromatography, and lectin chromatography. Various protein purification techniques are illustrated in *Current Protocols in Molecular Biology*, Ausubel et al., eds. (Wiley & Sons, New York, 1988, and quarterly updates).

"Selectable marker" refers to a marker that identifies a cell as having undergone a recombinant DNA or RNA event. Selectable markers include, for example, genes that encode antimetabolite resistance such as the DHFR protein that confers resistance to methotrexate (Wigler et al, 1980, *Proc Natl Acad Sci USA* 77:3567; O'Hare et al., 1981, *Proc Natl Acad Sci USA*, 78:1527), the GPT protein that confers resistance to mycophenolic acid (Mulligan & Berg, 1981, *PNAS USA*, 78:2072), the neomycin resistance marker that confers resistance to the aminoglycoside G-418 (Calberre-Garapin et al., 1981, *J Mol Biol*, 150:1), the Hygro protein that confers resistance to hygromycin (Santerre et al., 1984, *Gene* 30:147), and the Zeocin™ resistance marker (Invitrogen). In addition, the herpes simplex virus thymidine kinase, hypoxanthine-guanine phosphoribosyltransferase and adenine phosphoribosyltransferase genes can be employed in tk⁻, hgprt⁻ and aprt⁻ cells, respectively.

"Stringency" refers to the conditions (temperature, ionic strength, solvents, etc) under which hybridization between polynucleotides occurs. A hybridzation reaction conducted under high stringency conditions is one that will only occur between polynucleotide molecules that have a high degree of complementary base pairing (85% to 100% identity). Conditions for high stringency hybridization, for example, may include an overnight incubation at about 42° C. for about 2.5 hours in 6×SSC/0.1% SDS, followed by washing of the filters in 1.0×SSC at 65° C., 0.1% SDS. A hybridization reaction conducted under moderate stringency conditions is one that will occur between polynucleotide molecules that have an intermediate degree of complementary base pairing (50% to 84% identity).

"Substrate targeting moiety" refers to any signal on a substrate, either naturally occurring or genetically engineered, used to target any AviIII polypeptide or fragment thereof to a substrate. Such targeting moieties include ligands that bind to a substrate structure. Examples of ligand/receptor pairs include carbohydrate binding domains and cellulose. Many such substrate-specific ligands are known and are useful in the present invention to target an AviIII polypeptide or fragment thereof to a substrate. A novel example is an AviIII carbohydrate binding domain that is used to tether other molecules to a cellulose-containing substrate such as a fabric.

"Thermal tolerant" refers to the property of withstanding partial or complete inactivation by heat and can also be described as thermal resistance or thermal stability. Although some variation exists in the literature, the following definitions can be considered typical for the optimum temperature range of stability and activity for enzymes: psycrophilic (below freezing to 10 C); mesophilic (10° C. to 50° C.); thermophilic (50° C. to 75° C.); and caldophilic (75° C. to above boiling water temperature). The stability and catalytic activity of enzymes are linked characteristics, and the ways of measuring these properties vary considerably. For industrial enzymes, stability and activity are best measured under use conditions, often in the presence of substrate. Therefore, cellulases that must act on process streams of cellulose must be able to withstand exposure up to thermophilic or even caldophilic temperatures for digestion times in excess of several hours.

In encompassing a wide variety of potential applications for embodiments of the present invention, thermal tolerance refers to the ability to function in a temperature range of from about 15° C. to about 100° C. A preferred range is from about 30° C. to about 80° C. A highly preferred range is from about 50° C. to about 70° C. For example, a protein that can function at about 45° C. is considered in the preferred range even though it may be susceptible to partial or complete inactivation at temperatures in a range above about 45° C. and less than about 80° C. For polypeptides derived from organisms such as *Acidothermus*, the desirable property of thermal tolerance among is often accompanied by other desirable characteristics such as: resistance to extreme pH degradation, resistance to solvent degradation, resistance to proteolytic degradation, resistance to detergent degradation, resistance to oxidizing agent degradation, resistance to chaotropic agent degradation, and resistance to general degradation. Cowan D A in Danson M J et al. (1992) *The Archaebacteria. Biochemistry and Biotechnology* at 149-159, University Press, Cambridge, ISBN 1855780100. Here 'resistance' is intended to include any partial or complete level of residual activity. When a polypeptide is described as thermal tolerant it is understood that any one, more than one, or none of these other desirable properties can be present.

"Variant", as used herein, means a polynucleotide or polypeptide molecule that differs from a reference molecule. Variants can include nucleotide changes that result in amino acid substitutions, deletions, fusions, or truncations in the resulting variant polypeptide when compared to the reference polypeptide.

"Vector," "extra-chromosomal vector" or "expression vector" refers to a first polynucleotide molecule, usually double-stranded, which may have inserted into it a second polynucleotide molecule, for example a foreign or heterologous polynucleotide. The heterologous polynucleotide molecule may or may not be naturally found in the host cell, and may be, for example, one or more additional copy of the heterologous polynucleotide naturally present in the host genome. The vector is adapted for transporting the foreign polynucleotide molecule into a suitable host cell. Once in the host cell, the vector may be capable of integrating into the host cell chromosomes. The vector may optionally contain additional elements for selecting cells containing the integrated polynucleotide molecule as well as elements to promote transcription of mRNA from transfected DNA. Examples of vectors useful in the methods of the present invention include, but are not limited to, plasmids, bacteriophages, cosmids, retroviruses, and artificial chromosomes.

Within the application, unless otherwise stated, the techniques utilized may be found in any of several well-known references, such as: *Molecular Cloning: A Laboratory Manual* (Sambrook et al. (1989) Molecular cloning: A Laboratory Manual), *Gene Expression Technology* (Methods in Enzymology, Vol. 185, edited by D. Goeddel, 1991 Academic Press, San Diego, Calif.), "Guide to Protein Purification" in *Methods in Enzymology* (M. P. Deutshcer, 3d., (1990) Academic Press, Inc.), *PCR Protocols: A Guide to Methods and Applications* (Innis et al. (1990) Academic Press, San Diego, Calif.), Culture of Animal Cells: A Manual of Basic Technique, $2^{nd}$ ed. (R. I. Freshney (1987) Liss, Inc., New York, N.Y.), and *Gene Transfer and Expression Protocols*, pp 109-128, ed. E. J. Murray, The Humana Press Inc., Clifton, N.J.).

O-Glycoside Hydrolases:

Glycoside hydrolases are a large and diverse family of enzymes that hydrolyse the glycosidic bond between two carbohydrate moieties or between a carbohydrate and a non-carbohydrate moiety (See FIG. 2). Glycoside hydrolase enzymes are classified into glycoside hydrolase (GH) families based on significant amino acid similarities within their catalytic domains. Enzymes having related catalytic domains are grouped together within a family, (Henrissat et al., (1991) supra, and Henrissat et al. (1996), Biochem. J. 316:695-696), where the underlying classification provides a direct relationship between the GH domain amino acid sequence and how a GH domain will fold. This information ultimately provides a common mechanism for how the enzyme will hydrolyse the glycosidic bond within a substrate, i.e., either by a retaining mechanism or inverting mechanism (Henrissat., B, (1991) supra).

Cellulases belong to the GH family of enzymes. Cellulases are produced by a variety of bacteria and fungi to degrade the β-1,4 glycosidic bond of cellulose and to so produce successively smaller fragments of cellulose and ultimately produce glucose. At present, cellulases are found within are at least 11 different GH families. Three different types of cellulase enzyme activities have been identified within these GH families: exo-acting cellulases which cleave successive disaccharide units from the non-reducing ends of a cellulose chain; endo-acting cellulases which randomly cleave successive disaccharide units within the cellulose chain; and β-glucosidases which cleave successive disaccharide units to glucose (J. W. Deacon, (1997) Modern Mycology, 3rd Ed., ISBN: 0-632-03077-1, 97-98).

Many cellulases are characterized by having a multiple domain unit within their overall structure, a GH or catalytic domain is joined to a carbohydrate-binding domain (CBD) by a glycosylated linker peptide (Koivula et al., (1996) Protein Expression and Purification 8:391-400). As noted above, cellulases do not belong to any one family of GH domains, but rather have been identified within at least 11 different GH families to date. The CBD type domain increases the concentration of the enzyme on the substrate, in this case cellulose, and the linker peptide provides flexibility for both larger domains.

Conversion of cellulose to glucose is an essential step in the production of ethanol or other biofuels from biomass. Cellulases are an important component of this process, where approximately one kilogram of cellulase can digest fifty kilograms of cellulose. Within this process, thermostable cellulases have taken precedent, due to their ability to function at elevated temperatures and under other conditions including pH extremes, solvent presence, detergent presence, proteolysis, etc. (see Cowan D A (1992), supra).

Highly thermostable cellulase enzymes are secreted by the cellulolytic themophile *Acidothermus cellulolyticus* (U.S. Pat. Nos. 5,275,944 and 5,110,735). This bacterium was originally isolated from decaying wood in an acidic, thermal pool at Yellowstone National Park and deposited with the American Type Culture Collection (ATCC 43068) (Mohagheghi et al., (1986) *Int. J. System. Bacterial.*, 36:435-443).

Recently, a thermostable cellulase, E1 endoglucanase, was identified and characterized from *Acidothermus cellulolyticus* (U.S. Pat. No. 5,536,655). The E1 endoglucanase has maximal activity between 75 and 83° C. and is active to a pH well below 5. Thermostable cellulase, and E1 endoglucanase, are useful in the conversion of biomass to biofuels, and in particular, are useful in the conversion of cellulose to glucose. Conversion of biomass to biofuel represents an extremely important alternative fuel source that is more environmentally friendly than conventional fuels, and provides a use, in some cases, for waste products.

AviIII:

As described more fully in the Examples below, AviIII, a novel thermostable cellulase, has now been identified and characterized. The predicted amino acid sequence of AviIII (SEQ ID NO:1) has an organization characteristic of a cellulase enzyme. AviIII contains a catalytic domain—carbohydrate binding domain unit. In particular, AviIII includes a GH74 catalytic domain (amino acids from about A47 to about G786), and a carbohydrate binding domain type III (CBDIII) (amino acids from about V869 to about at least Q956).

As discussed in more detail below (Example 2), significant amino acid similarity of AviIII to other cellulases identifies AviIII as a cellulase. In addition, the predicted amino acid sequence (SEQ ID NO: 1) indicates that a CBD type III domain is present as characterized by Tomme P. et al. (1995), in Enzymatic Degradation of Insoluble Polysaccharides (Saddler J N & Penner M, eds.), at 142-163, American Chemical Society, Washington. See also Tomme, P. & Claeyssens, M. (1989) FEBS Lett. 243, 239243; Gilkes, N. R et al., (1988) J. Biol. Chem. 263, 10401-10407.

AviIII, as noted above, has a catalytic domain, identified as belonging to the GH74 family. The GH74 domain family includes an avicelase from *Aspergillus aculeatus*.

AviIII is also a thermostable cellulase as it is produced by the themophile *Acidothermus cellulolyticus*. As discussed, AviIII polypeptides can have other desirable characteristics (see Cowan D A (1992), supra). Like other members of the cellulase family, and in particular thermostable cellulases, AviIII polypeptides are useful in the conversion of biomass to biofuels and biofuel additives, and in particular, biofuels from cellulose. It is envisioned that AviIII polypeptides could be used for other purposes, for example in detergents, pulp and paper processing, food and feed processing, and in textile processes. AviIII polypeptides can be used alone or in combination with one or more other cellulases or glycoside hydrolases to perform the uses described herein or known within the relevant art, all of which are within the scope of the present disclosure.

AviIII Polypeptides:

AviIII polypeptides of the invention include isolated polypeptides having an amino acid sequence as shown below in Example 1; Table 3 and in SEQ ID NO:1, as well as variants and derivatives, including fragments, having substantial identity to the amino acid sequence of SEQ ID NO:1 and that retain any of the functional activities of AviIII. AviIII polypeptide activity can be determined, for example, by subjecting the variant, derivative, or fragment to a substrate binding assay or a cellulase activity assay such as those described in Irwin D et al., J. Bacteriology 180(7): 1709-1714 (April 1998).

TABLE 3

AviIII amino acid sequence. (SEQ ID NO: 1)

MDRSENIRLTMRSRRLVSLLAATASFAVAAALGVLPIAITASPAHAATTQ

PYTWSNVAIGGGGFVDGIVFNEGAPGILYVRTDIGGMYRWDAANGRWIPL

LDWVGWNNWGYNGVVSIAADPINTNKVWAAVGMYTNSWDPNDGAILRSSD

QGATWQITPLPFKLGGNMPGRGMGERLAVDPNNDNILYFGAPSGKGLWRS

TDSGATWSQMTNFPDVGTYIANPTDTTGYQSDIQGVVWVAFDKSSSSLGQ

ASKTIFVGVADPNNPVFWSRDGGATWQAVPGAPTGFIPHKGVFDPVNGVL

YIATSNTGGPYDGSSGDVWKFSVTSGTWTRISPVPSTDTANDYFGYSGLT

IDRQHPNTIMVATQISWWPDTIIFRSTDGGATWTRIWDWTSYPNRSLRYV

LDISAEPWLTFGVQPNPPVPSPKLGWMDEAMAIDPFNSDRMLYGRGATLY

ATNDLTKWDSGGQIGIAPMVKGLEETAVNDLISPPSGAPLISALGDLGGF

THADVTAVPSTIFTSPVFTTGTSVDYAELNPSIIVRAGSFDPSSQPNDRH

VAFSTDGGKNWFQGSEPGGVTTGGTVAASADGSRFVWAPGDPGQPVVYAV

GFGNSWAASQGVPANAQIRSDRVNPKTFYALSNGTFYRSTDGGVTFQPVA

AGLPSSGAVGVMFHAVPGKEGDLWLAASSGLYHSTNGGSSWSAITGVSSA

VNVGFGKSAPGSSYPAVFVVGTIGGVTGAYRSDDCGTTWVLINDDQHQYG

NWGQAITGDHANLRRVYIGTNGRGIVYGDIGGAPSGSPSPSVSPSASPSL

SPSPSPSSSSPSPSPSPSSSPSSSPSPSPSPSPSPSRSPSPSASPSPSSSP

SPSSSPSSSPSPTPSSSPVSGGVKVQYKNNDSAPGDNQIKPGLQVVNTGS

SSVDLSTVTVRYWFTRDGGSSTLVYNCDWAAIGCGNIRASFGSVNPATPA

ADTYLQX*

As listed and described in Tables 3 and 2, the isolated AviIII polypeptide includes an N-terminal hydrophobic region that functions as a signal peptide, having an amino acid sequence that begins with Met11 and extends to about A46, a catalytic domain having significant sequence similarity to a GH74 family domain that begins with about A47 and extends to about G786, a carbohydrate binding domain having sequence similarity to such type III domains that begins with about V869 and extends to about at least Q956. Variants and derivatives of AviIII include, for example, AviIII polypeptides modified by covalent or aggregative conjugation with other chemical moieties, such as glycosyl groups, polyethylene glycol (PEG) groups, lipids, phosphate, acetyl groups, and the like.

The amino acid sequence of AviIII polypeptides of the invention is preferably at least about 60% identical, more preferably at least about 70% identical, or in some embodiments at least about 90% identical, to the AviIII amino acid sequence shown above Table 3 and SEQ ID NO:1. The percentage identity, also termed homology (see definition above) can be readily determined, for example, by comparing the two polypeptide sequences using any of the computer programs commonly employed for this purpose, such as the Gap program (Wisconsin Sequence Analysis Package, Version 8 for Unix, Genetics Computer Group, University Research Park, Madison Wis.), which uses the algorithm of Smith and Waterman, 1981, Adv. Appl. Math. 2: 482-489.

Variants and derivatives of the AviIII polypeptide may further include, for example, fusion proteins formed of a AviIII polypeptide and a heterologous polypeptide. Preferred heterologous polypeptides include those that facilitate purification, oligomerization, stability, or secretion of the AviIII polypeptides.

AviIII polypeptide variants and derivatives, as used in the description of the invention, can contain conservatively substituted amino acids, meaning that one or more amino acid can be replaced by an amino acid that does not alter the secondary and/or tertiary structure of the polypeptide. Such substitutions can include the replacement of an amino acid, by a residue having similar physicochemical properties, such as substituting one aliphatic residue (Ile, Val, Leu, or Ala) for another, or substitutions between basic residues Lys and Arg, acidic residues Glu and Asp, amide residues Gln and Asn, hydroxyl residues Ser and Tyr, or aromatic residues Phe and Tyr. Phenotypically silent amino acid exchanges are described more fully in Bowie et al., 1990, Science 247:1306-1310. In addition, functional AviIII polypeptide variants include those having amino acid substitutions, deletions, or additions to the amino acid sequence outside functional regions of the protein, for example, outside the catalytic and carbohydrate binding domains. These would include, for example, the various linker sequences that connect functional domains as defined herein.

The AviIII polypeptides of the present invention are preferably provided in an isolated form, and preferably are substantially purified. The polypeptides may be recovered and purified from recombinant cell cultures by known methods, including, for example, ammonium sulfate or ethanol precipitation, anion or cation exchange chromatography, phosphocellulose chromatography, hydrophobic interaction chromatography, affinity chromatography, hydroxylapatite chromatography, and lectin chromatography. Preferably, high performance liquid chromatography (HPLC) is employed for purification.

Another preferred form of AviIII polypeptides is that of recombinant polypeptides as expressed by suitable hosts. Furthermore, the hosts can simultaneously produce other cellulases such that a mixture is produced comprising a AviIII polypeptide and one or more other cellulases. Such a mixture can be effective in crude fermentation processing or other industrial processing.

AviIII polypeptides can be fused to heterologous polypeptides to facilitate purification. Many available heterologous peptides (peptide tags) allow selective binding of the fusion protein to a binding partner. Non-limiting examples of peptide tags include 6-His, thioredoxin, hemaglutinin, GST, and the OmpA signal sequence tag. A binding partner that recognizes and binds to the heterologous peptide can be any molecule or compound, including metal ions (for example, metal affinity columns), antibodies, antibody fragments, or any protein or peptide that preferentially binds the heterologous peptide to permit purification of the fusion protein.

AviIII polypeptides can be modified to facilitate formation of AviIII oligomers. For example, AviIII polypeptides can be fused to peptide moieties that promote oligomerization, such as leucine zippers and certain antibody fragment polypeptides, for example, Fc polypeptides. Techniques for preparing these fusion proteins are known, and are described, for example, in WO 99/31241 and in Cosman et. al., 2001 *Immunity* 14:123-133. Fusion to an Fc polypeptide offers the additional advantage of facilitating purification by affinity chromatography over Protein A or Protein G columns. Fusion to a leucine-zipper (LZ), for example, a repetitive heptad repeat, often with four or five leucine residues interspersed with other amino acids, is described in Landschultz et al., 1988, *Science,* 240:1759.

It is also envisioned that an expanded set of variants and derivatives of AviIII polynucleotides and/or polypeptides can be generated to select for useful molecules, where such expansion is achieved not only by conventional methods such as site-directed mutagenesis (SDM) but also by more modern techniques, either independently or in combination.

Site-directed-mutagenesis is considered an informational approach to protein engineering and can rely on high-resolution crystallographic structures of target proteins and some stratagem for specific amino acid changes (Van Den Burg, B.; Vriend, G.; Veltman, O. R.; Venema, G.; Eijsink, V. G. H. Proc. Nat. Acad. Sci. U.S. 1998, 95, 2056-2060). For example, modification of the amino acid sequence of AviIII polypeptides can be accomplished as is known in the art, such as by introducing mutations at particular locations by oligonucleotide-directed mutagenesis (Walder et al., 1986, Gene, 42:133; Bauer et al., 1985, Gene 37:73; Craik, 1985, BioTechniques, 12-19; Smith et al., 1981, Genetic Engineering: Principles and Methods, Plenum Press; and U.S. Pat. No. 4,518,584 and U.S. Pat. No. 4,737,462). SDM technology can also employ the recent advent of computational methods for identifying site-specific changes for a variety of protein engineering objectives (Hellinga, H. W. Nature Structural. Biol. 1998, 5, 525-527).

The more modern techniques include, but are not limited to, non-informational mutagenesis techniques (referred to generically as "directed evolution"). Directed evolution, in conjunction with high-throughput screening, allows testing of statistically meaningful variations in protein conformation (Arnold, F. H. Nature Biotechnol. 1998, 16, 617-618). Directed evolution technology can include diversification methods similar to that described by Crameri A. et al. (1998, Nature 391: 288-291), site-saturation mutagenesis, staggered extension process (StEP) (Zhao, H.; Giver, L.; Shao, Z.; Affholter, J. A.; Arnold, F. H. Nature Biotechnol. 1998, 16, 258-262), and DNA synthesis/reassembly (U.S. Pat. No. 5,965,408).

Fragments of the AviIII polypeptide can be used, for example, to generate specific anti-AviIII antibodies. Using known selection techniques, specific epitopes can be selected and used to generate monoclonal or polyclonal antibodies. Such antibodies have utlilty in the assay of AviIII activity as well as in purifying recombinant AviIII polypeptides from genetically engineered host cells.

AviIII Polynucleotides:

The invention also provides polynucleotide molecules encoding the AviIII polypeptides discussed above. AviIII polynucleotide molecules of the invention include polynucleotide molecules having the nucleic acid sequence shown in Table 4 and SEQ ID NO: 2, polynucleotide molecules that hybridize to the nucleic acid sequence of Table 4 and SEQ ID NO:2 under high stringency hybridization conditions (for example, 42° C., 2.5 hr., 6×SCC, 0.1% SDS); and polynucleotide molecules having substantial nucleic acid sequence identity with the nucleic acid sequence of Table 4 and SEQ ID NO:2, particularly with those nucleic acids encoding the catalytic domain, GH74 (from about amino acid A47 to about G786), the carbohydrate binding domain III (from about amino acid V869 to about at least Q956).

TABLE 4

AviIII nucleotide sequence. (SEQ ID NO: 2)

ATGGATCGTTCGGAGAACATCCGTCTGACTATGAGATCACGACGATTGGT
ATCACTGCTCGCCGCCACTGCGTCGTTCGCCGTGGCCGCCGCTCTGGGAG
TTCTGCCCATCGCGATAACGGCTTCTCCTGCGCACGCGGCGACGACTCAG
CCGTACACCTGGAGCAACGTGGCGATCGGGGCGGCGGCTTTGTCGACGG
GATCGTCTTCAATGAAGGTGCACCGGGAATTCTGTACGTGCGGACGGACA
TCGGGGGATGTATCGATGGGATGCCGCCAACGGGCGGTGGATCCCTCTT
CTGGATTGGGTGGGATGGAACAATTGGGGGTACAACGGCGTCGTCAGCAT
TGCGGCAGACCCGATCAATACTAACAAGGTATGGGCCGCCGTCGGAATGT
ACACCAACAGCTGGGACCCAAACGACGGAGCGATTCTCCGCTCGTCTGAT
CAGGGCGCAACGTGGCAAATAACGCCCCTGCCGTTCAAGCTTGGCGGCAA
CATGCCCGGGCGTGGAATGGGCGAGCGGCTTGCGGTGGATCCAAACAATG
ACAACATTCTGTATTTCGGCGCCCGAGCGGCAAAGGGCTCTGGAGAAGC
ACAGATTCCGGCGCGACCTGGTCCCAGATGACGAACTTTCCGGACGTAGG
CACGTACATTGCAAATCCCACTGACACGACCGGCTATCAGAGCGATATTC
AAGGCGTCGTCTGGGTCGCTTTCGACAAGTCTTCGTCATCGCTCGGGCAA
GCGAGTAAGACCATTTTTGTGGGCGTGGCGGATCCCAATAATCCGGTCTT
CTGGAGCAGAGACGGCGGCGCGACGTGGCAGGCGGTGCCGGGTGCGCCGA
CCGGCTTCATCCCGCACAAGGGCGTCTTTGACCCGGTCAACCACGTGCTC
TATATTGCCACCAGCAATACGGGTGGTCCGTATGACGGGAGCTCCGGCGA
CGTCTGGAAATTCTCGGTGACCTCCGGGACATGGACGCGAATCAGCCCGG
TACCTTCGACGGACACGGCCAACGACTACTTTGGTTACAGCGGCCTCACT
ATCGACCGCCAGCACCCGAACACGATAATGGTGGCAACCCAGATATCGTG
GTGGCCGGACACCATAATCTTTCGGAGCACCGACGGCGGTGCGACGTGGA
CGCGGATCTGGGATTGGACGAGTTATCCCAATCGAAGCTTGCGATATGTG
CTTGACATTTCGGCGGAGCCTTGGCTGACCTTCGGCGTACAGCCGAATCC
TCCCGTACCCAGTCCGAAGCTCGGCTGGATGGATGAAGCGATGGCAATCG
ATCCGTTCAACTCTGATCGGATGCTCTACGGAACAGGCGCGACGTTGTAC
GCAACAAATGATCTCACGAAGTGGGACTCCGGCGGCCAGATTCATATCGC
GCCGATGGTCAAAGGATTGGAGGAGACGGCGGTAAACGATCTCATCAGCC
CGCCGTCTGGCGCCCCGCTCATCAGCGCTCTCGGAGACCTCGGCGGCTTC
ACCCACGCCGACGTTACTGCCGTGCCATCGACGATCTTCACGTCACCGGT
GTTCACGACCGGCACCAGCGTCGACTATGCGGAATTGAATCCGTCGATCA
TCGTTCGCGCTGGAAGTTTCGATCCATCGAGCCAACCGAACGACAGGCAC
GTCGCGTTCTCGACAGACGGCGGCAAGAACTGGTTCCAAGGCAGCGAACC

TABLE 4-continued

AviIII nucleotide sequence. (SEQ ID NO: 2)

TGGCGGGGTGACGACGGGCGGCACCGTCGCCGCATCGGCCGACGGCTCTC
GTTTCGTCTGGGCTCCCGGCGATCCCGGTCAGCCTGTGGTGTACGCAGTC
GGATTTGGCAACTCCTGGGCTGCTTCGCAAGGTGTTCCCGCCAATGCCCA
GATCCGCTCAGACCGGGTGAATCCAAAGACTTTCTATGCCCTATCCAATG
GAACCTTCTATCGAAGCACGGACGGCGGCGTGACATTCCAACCGGTCGCG
GCCGGTCTTCCGAGCAGCGGTGCCGTCGGTGTCATGTTCCACGCGGTGCC
TGGAAAAGAAGGCGATCTGTGGCTCGCTGCATCGAGCGGGCTTTACCACT
CAACCAATGGCGGCAGCAGTTGGTCTGCAATCACCGGCGTATCCTCCGCG
GTGAACGTGGGATTTGGTAAGTCTGCGCCCGGGTCGTCATACCCAGCCGT
CTTTGTCGTCGGCACGATCGGAGGCGTTACGGGGGCGTACCGCTCCGACG
ACTGTGGGACGACCTGGGTACTGATCAATGATGACCAGCACCAATACGGA
AATTGGGGACAAGCAATCACCGGTGACCACGCGAATTTACGGCGGGTGTA
CATAGGCACGAACGGCCGTGGAATTGTATACGGGGACATTGGTGGTGCGC
CGTCCGGATCGCCGTCTCCGTCGGTGAGTCCGTCGGCTTCGCCGAGCCTG
AGCCCGAGCCCGAGCCCGAGCAGCTCGCCATCGCCGTCGCCGTCGCCGAG
CTCGACTCCATCCTCGTCGCCGTCTCCGTCGCCGTCACCATCGCCGAGTC
CGTCTCCCTCTCCGTCACCATCGGCGTCGCCGAGCCCGTCTTCGTCACCG
AGCCCGTCTTCGTCACCGTCTTCGTCGCCGAGCCCAACGCCGTCGTCGTC
GCCGGTGTCGGGTGGGGTGAAGGTGCAGTATAAGAATAATGATTCGGCGC
CGGGTGATAATCAGATCAAGCCCGGTTTGCAGGTGGTGAATACCGGGTCG
TCGTCGGTGGATTTGTCGACGGTGACGGTGCGGTACTGGTTCACCCGGGA
TGGTGCCTCGTCGACACTGGTGTACMCTGTGACTGGGCGGCGATCGGGTG
TGGGAAATATCCGCGCCTCGTTCGGCTCGGTGAACCCGGCGACGCCGACG
GCGGACACCTACCTGCAGN*

The AviIII polynucleotide molecules of the invention are preferably isolated molecules encoding the AviIII polypetide having an amino acid sequence as shown in Table 3 and SEQ ID NO:1, as well as derivatives, variants, and useful fragments of the AviIII polynucleotide. The AviIII polynucleotide sequence can include deletions, substitutions, or additions to the nucleic acid sequence of Table 4 and SEQ ID NO: 2.

The AviIII polynucleotide molecule of the invention can be cDNA, chemically synthesized DNA, DNA amplified by PCR, RNA, or combinations thereof. Due to the degeneracy of the genetic code, two DNA sequences may differ and yet encode identical amino acid sequences. The present invention thus provides an isolated polynucleotide molecule having a AviIII nucleic acid sequence encoding AviIII polypeptide, where the nucleic acid sequence encodes a polypeptide having the complete amino acid sequences as shown in Table 3 and SEQ ID NO: 1, or variants, derivatives, and fragments thereof.

The AviIII polynucleotides of the invention have a nucleic acid sequence that is at least about 60% identical to the nucleic acid sequence shown in Table 4 and SEQ ID NO: 2, in some embodiments at least about 70% identical to the nucleic acid sequence shown in Table 4 and SEQ ID NO: 2, and in other embodiments at least about 90% identical to the nucleic acid sequence shown in Table 4 and SEQ ID NO: 2. Nucleic acid sequence identity is determined by known methods, for example by aligning two sequences in a software program such as the BLAST program (Altschul, S. F et al. (1990) J. Mol. Biol. 215:403-410.)

The AvilII polynucleotide molecules of the invention also include isolated polynucleotide molecules having a nucleic acid sequence that hybridizes under high stringency conditions (as defined above) to a the nucleic acid sequence shown in Table 4 and SEQ ID NO: 2. Hybridization of the polynucleotide is to about 15 contiguous nucleotides, or about 20 contiguous nucleotides, and in other embodiments about 30 contiguous nucleotides, and in still other embodiments about 100 contiguous nucleotides of the nucleic acid sequence shown in Table 4 and SEQ ID NO: 2.

Useful fragments of the AvilII-encoding polynucleotide molecules described herein, include probes and primers. Such probes and primers can be used, for example, in PCR methods to amplify and detect the presence of AvilII polynucleotides in vitro, as well as in Southern and Northern blots for analysis of AvilII. Cells expressing the AvilII polynucleotide molecules of the invention can also be identified by the use of such probes. Methods for the production and use of such primers and probes are known. For PCR, 5' and 3' primers corresponding to a region at the termini of the AvilII polynucleotide molecule can be employed to isolate and amplify the AvilII polynucleotide using conventional techniques.

Other useful fragments of the AvilII polynucleotides include antisense or sense oligonucleotides comprising a single-stranded nucleic acid sequence capable of binding to a target AvilII mRNA (using a sense strand), or DNA (using an antisense strand) sequence.

Vectors and Host Cells:

The present invention also provides vectors containing the polynucleotide molecules of the invention, as well as host cells transformed with such vectors. Any of the polynucleotide molecules of the invention may be contained in a vector, which generally includes a selectable marker and an origin of replication, for propagation in a host. The vectors further include suitable transcriptional or translational regulatory sequences, such as those derived from a mammalian, microbial, viral, or insect genes, operably linked to the AvilII polynucleotide molecule. Examples of such regulatory sequences include transcriptional promoters, operators, or enhancers, mRNA ribosomal binding sites, and appropriate sequences which control transcription and translation. Nucleotide sequences are operably linked when the regulatory sequence functionally relates to the DNA encoding the target protein. Thus, a promoter nucleotide sequence is operably linked to a AvilII DNA sequence if the promoter nucleotide sequence directs the transcription of the AvilII sequence.

Selection of suitable vectors for the cloning of AvilII polynucleotide molecules encoding the target AvilII polypeptides of this invention will depend upon the host cell in which the vector will be transformed, and, where applicable, the host cell from which the target polypeptide is to be expressed. Suitable host cells for expression of AvilII polypeptides include prokaryotes, yeast, and higher eukaryotic cells, each of which is discussed below.

The AvilII polypeptides to be expressed in such host cells may also be fusion proteins that include regions from heterologous proteins. As discussed above, such regions may be included to allow, for example, secretion, improved stability, or facilitated purification of the AvilII polypeptide. For example, a nucleic acid sequence encoding an appropriate signal peptide can be incorporated into an expression vector. A nucleic acid sequence encoding a signal peptide (secretory leader) may be fused in-frame to the AvilII sequence so that AvilII is translated as a fusion protein comprising the signal peptide. A signal peptide that is functional in the intended host cell promotes extracellular secretion of the AvilII polypeptide. Preferably, the signal sequence will be cleaved from the AvilII polypeptide upon secretion of AvilII from the cell. Non-limiting examples of signal sequences that can be used in practicing the invention include the yeast I-factor and the honeybee melatin leader in Sf9 insect cells.

Suitable host cells for expression of target polypeptides of the invention include prokaryotes, yeast, and higher eukaryotic cells. Suitable prokaryotic hosts to be used for the expression of these polypeptides include bacteria of the genera *Escherichia, Bacillus,* and *Salmonella*, as well as members of the genera *Pseudomonas, Streptomyces,* and *Staphylococcus.* For expression in prokaryotic cells, for example, in *E. coli*, the polynucleotide molecule encoding AvilII polypeptide preferably includes an N-terminal methionine residue to facilitate expression of the recombinant polypeptide. The N-terminal Met may optionally be cleaved from the expressed polypeptide.

Expression vectors for use in prokaryotic hosts generally comprise one or more phenotypic selectable marker genes. Such genes encode, for example, a protein that confers antibiotic resistance or that supplies an auxotrophic requirement. A wide variety of such vectors are readily available from commercial sources. Examples include pSPORT vectors, pGEM vectors (Promega, Madison, Wis.), pPROEX vectors (LTI, Bethesda, Md.), Bluescript vectors (Stratagene), and pQE vectors (Qiagen).

AvilII can also be expressed in yeast host cells from genera including *Saccharomyces, Pichia,* and *Kluveromyces*. Preferred yeast hosts are *S. cerevisiae* and *P. pastoris*. Yeast vectors will often contain an origin of replication sequence from a 2T yeast plasmid, an autonomously replicating sequence (ARS), a promoter region, sequences for polyadenylation, sequences for transcription termination, and a selectable marker gene. Vectors replicable in both yeast and *E. coli* (termed shuttle vectors) may also be used. In addition to the above-mentioned features of yeast vectors, a shuttle vector will also include sequences for replication and selection in *E. coli*. Direct secretion of the target polypeptides expressed in yeast hosts may be accomplished by the inclusion of nucleotide sequence encoding the yeast I-factor leader sequence at the 5' end of the AvilII-encoding nucleotide sequence.

Insect host cell culture systems can also be used for the expression of AvilII polypeptides. The target polypeptides of the invention are preferably expressed using a baculovirus expression system, as described, for example, in the review by Luckow and Summers, 1988 *Bio/Technology* 6:47.

The choice of a suitable expression vector for expression of AvilII polypeptides of the invention will depend upon the host cell to be used. Examples of suitable expression vectors for *E. coli* include pET, pUC, and similar vectors as is known in the art. Preferred vectors for expression of the AvilII polypeptides include the shuttle plasmid pIJ702 for *Streptomyces lividans*, pGAPZalpha-A, B, C and pPICZalpha-A, B, C (Invitrogen) for *Pichia pastoris*, and pFE-1 and pFE-2 for filamentous fungi and similar vectors as is known in the art.

Modification of a AvilII polynucleotide molecule to facilitate insertion into a particular vector (for example, by modifying restriction sites), ease of use in a particular expression system or host (for example, using preferred host codons), and the like, are known and are contemplated for use in the invention. Genetic engineering methods for the production of AviIII polypeptides include the expression of the polynucleotide molecules in cell free expression systems, in cellular hosts, in tissues, and in animal models, according to known methods.

Compositions

The invention provides compositions containing a substantially purified AviIII polypeptide of the invention and an acceptable carrier. Such compositions are administered to biomass, for example, to degrade the cellulose in the biomass into simpler carbohydrate units and ultimately, to sugars. These released sugars from the cellulose are converted into ethanol by any number of different catalysts. Such compositions may also be included in detergents for removal, for example, of cellulose containing stains within fabrics, or compositions used in the pulp and paper industry, to address conditions associated with cellulose content. Compositions of the present invention can be used in stonewashing jeans such as is well known in the art. Compositions can be used in the biopolishing of cellulosic fabrics, such as cotton, linen, rayon and Lyocell.

The invention provides pharmaceutical compositions containing a substantially purified AviIII polypeptide of the invention and if necessary a pharmaceutically acceptable carrier. Such pharmaceutical compositions are administered to cells, tissues, or patients, for example, to aid in delivery or targeting of other pharmaceutical compositions. For example, AviIII polypeptides may be used where carbohydrate-mediated liposomal interactions are involved with target cells. Sihorkar, V. et al. (2001), J. Pharmacy & Pharmaceutical Sciences May-August 4(2): 138-58.

The invention also provides reagents, compositions, and methods that are useful for analysis of AviIII activity and for the analysis of cellulose breakdown.

Compositions of the present invention may also include other known cellulases, and preferably, other known thermal tolerant cellulases for enhanced treatment of cellulose.

Antibodies

The polypeptides of the present invention, in whole or in part, may be used to raise polyclonal and monoclonal antibodies that are useful in purifying AviIII, or detecting AviIII polypeptide expression, as well as a reagent tool for characterizing the molecular actions of the AviIII polypeptide. Preferably, a peptide containing a unique epitope of the AviIII polypeptide is used in preparation of antibodies, using conventional techniques. Methods for the selection of peptide epitopes and production of antibodies are known. See, for example, *Antibodies: A Laboratory Manual*, Harlow and Land (eds.), 1988 Cold Spring Harbor Laboratory Press, Cold Spring Harbor, N.Y.; *Monoclonal Antibodies, Hybridomas: A New Dimension in Biological Analyses*, Kennet et al. (eds.), 1980 Plenum Press, New York.

Assays

Agents that modify, for example, increase or decrease, AviIII hydrolysis or degradation of cellulose can be identified, for example, by assay of AviIII cellulase activity and/or analysis of AviIII binding to a cellulose substrate. Incubation of cellulose in the presence of AviIII and in the presence or absence of a test agent and correlation of cellulase activity or carbohydrate binding permits screening of such agents. For example, cellulase activity and binding assays may be performed in a manner similar to those described in Irwin et al., J. Bacteriology 180(7): 1709-1714 (April 1998).

The AviIII stimulated activity is determined in the presence and absence of a test agent and then compared. A lower AviIII activated test activity in the presence of the test agent, than in the absence of the test agent, indicates that the test agent has decreased the activity of the AviIII. A higher AviIII activated test activity in the presence of the test agent than in the absence of the test agent indicates that the test agent has increased the activity of the AviIII. Stimulators and inhibitors of AviIII may be used to augment, inhibit, or modify AviIII mediated activity, and therefore may have potential industrial uses as well as potential use in the further elucidation of AviIII's molecular actions.

Therapeutic Applications

The AviIII polypeptides of the invention are effective in adding in delivery or targeting of other pharmaceutical compositions within a host. For example, AviIII polypeptides may be used where carbohydrate-mediated liposomal interactions are involved with target cells. Sihorkar, V. et al. (2001), *J. Pharm Pharm Sci* May-August 4(2): 138-58.

AviIII polynucleotides and polypeptides, including vectors expressing AviIII, of the invention can be formulated as pharmaceutical compositions and administered to a host, preferably mammalian host, including a human patient, in a variety of forms adapted to the chosen route of administration. The compounds are preferably administered in combination with a pharmaceutically acceptable carrier, and may be combined with or conjugated to specific delivery agents, including targeting antibodies and/or cytokines.

AviIII can be administered by known techniques, such as orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleagenous suspensions or suppositories.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Preferred administration routes include orally, parenterally, as well as intravenous, intramuscular or subcutaneous routes. More preferably, the compounds of the present invention are administered parenterally, i.e., intravenously or intraperitoneally, by infusion or injection.

Solutions or suspensions of the compounds can be prepared in water, isotonic saline (PBS) and optionally mixed with a nontoxic surfactant. Dispersions may also be prepared in glycerol, liquid polyethylene, glycols, DNA, vegetable oils, triacetin and mixtures thereof. Under ordinary conditions of storage and use, these preparations may contain a preservative to prevent the growth of microorganisms.

The pharmaceutical dosage form suitable for injection or infusion use can include sterile, aqueous solutions or dispersions or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption—for example, aluminum monosterate hydrogels and gelatin.

Sterile injectable solutions are prepared by incorporating the compounds in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

INDUSTRIAL APPLICATIONS

The AviIII polypeptides of the invention are effective cellulases. In the methods of the invention, the cellulose degrading effects of AviIII are achieved by treating biomass at a ratio of about 1 to about 50, or about 1:40, 1:35, 1:30, 1:25, 1:20 or even about 1:70 in some preparations of the AVIIII of AviIII:biomass. AviIII may be used under extreme conditions, for example, elevated temperatures and acidic pH. Treated biomass is degraded into simpler forms of carbohydrates, and in some cases glucose, which is then used in the formation of ethanol or other industrial chemicals, as is known in the art. Other methods are envisioned to be within the scope of the present invention, including methods for treating fabrics to remove cellulose-containing stains and other methods already discussed. AviIII polypeptides can be used in any known application currently utilizing a cellulase, all of which are within the scope of the present invention.

Having generally described the invention, the same will be more readily understood by reference to the following examples, which are provided by way of illustration and are not intended as limiting.

EXAMPLES

Example 1

Molecular Cloning of AviIII

Genomic DNA was isolated from *Acidothermus cellulolyticus* and purified by banding on cesium chloride gradients. Genomic DNA was partially digested with Sau 3A and separated on agarose gels. DNA fragments in the range of 9-20 kilobase pairs were isolated from the gels. This purified Sau 3A digested genomic DNA was ligated into the Bam H1 acceptor site of purified EMBL3 lambda phage arms (Clontech, San Diego, Calif.). Phage DNA was packaged according to the manufacturer's specification and plated with *E. Coli* LE392 in top agar which contained the in soluble cellulose analog, carboxymethylcellulose (CMC). The plates were incubated overnight (12-24 hours) to allow transfection, bacterial growth, and plaque formation. Plates were stained with Congo Red followed by destaining with 1 M NaCl. Lambda plaques harboring endoglucanase clones showed up as unstained plaques on a red background.

Lambda clones which screened positive on CMC-Congo Red plates were purified by successive rounds of picking, plating and screening. Individual phage isolates were named SL-1, SL-2, SL-3, and SL-4. Subsequent subcloning efforts employed the SL-3 clone which contained an approximately 14.2 kilobase fragment of *Acidothermus cellulolyticus* genomic DNA.

Template DNA was constructed using a 9 kilobase Bam H1 fragment obtained from the 14.2 kilobase lambda clone SL-3 prepared from *Acidothermus cellulolyticus* genomic DNA. The 9 kilobase Bam H1 fragment from SL-3 was subcloned into pDR540 to generate a plasmid NREL501. NREL501 was sequenced by the primer walking method as is known in the art. NREL501 was then subcloned into pUC19 using restriction enzymes Pst I and Eco RI and transformed into *E. coli* XL1-blue (Stratagene) for the production of template DNA for sequencing. Each subclone was sequenced from both the forward and reverse directions. DNA for sequencing was prepared from an overnight growth in 500 mL LB broth using a megaprep DNA purification kit from Promega. The templated DNA was PEG precipitated and suspended in de-ionized water and adjusted to a final concentration of 0.25 milligrams/mL.

Custom primers were designed by reading upstream known sequence and selecting segments of an appropriate length to function, as is well known in the art. Primers for cycle sequencing were synthesized at the Macromolecular Resources Facility located at Colorado State University in Fort Collins, Colo. Typically the sequencing primers were 26 to 30 nucleotides in length, but were sometimes longer or shorter to accommodate a melting temperature appropriate for cycle sequencing. The sequencing primers were diluted in de-ionized water, the concentration measured using UV absorbance at 260 nm, and then adjusted to a final concentration of 5 pmol/microL.

Templates and sequencing primers were shipped to the Iowa State University DNA Sequencing Facility at Ames, Iowa for sequencing using standard chemistries for cycle sequencing. In some cases, regions of the template that sequenced poorly using the standard protocols and dye terminators were repeated with the addition of 2 microL DMSO and by using nucleotides optimized for the sequencing of high GC content DNA. An inverse PCR technique known in the art was applied to continue sequencing the genomic DNA, and a primer walking method was used to sequence the large PCR products. Each PCR fragment was sequenced from both strands, using high fidelity commercial DNA polymerase.

Sequencing data from primer walking and subclones were assembled together to verify that all SL-3 regions had been sequenced from both strands. An open reading frame (ORF) was found in the 9 kilobase Barn H1 fragment, C-terminal of E1 (U.S. Pat. No. 5,536,655), termed AviIII. An ORF of about 3 kb (SEQ ID NO:2) and deduced amino acid sequence (SEQ ID NO:1) are shown in Tables 3 and 4. The amino acid sequence predicted by SEQ ID NO:1 was determined to have significant homology to known cellulases, as is shown below in Example 2 and Table 5.

The amino acid sequence represents a novel member of the family of proteins with cellulase activity. Due to the source of isolation, from the thermophilic *Acidothermus cellulolyticus*, AviIII is a novel member of cellulases with properties including thermal tolerance. It is also known that thermal tolerant enzymes may have other properties (see definition above).

Example 2

AviIII Includes a GH74 Catalytic Domain

Sequence alignments and comparisons of the amino acid sequences of the *Acidothermus cellulolyticus* AviIII catalytic domain (approximately amino acids 47 to 786) and *Aspergillus aculeatus* Avicelase III (endoglucanase) polypeptides were prepared, using the ClustalW program (See Thompson J. D et al. (1994), Nucleic Acids Res. 22:4673-4680). An examination of the amino acid sequence alignment of the GH74 domain indicates that the amino acid sequence of AviIII catalytic domain is homologous to the amino acid sequence of a known GH74 family catalytic domains for *Aspergillus aculeatus* Avicelase III (endoglucanase) (see Table 5). In Table 5, the notations are as follows: an asterisk "*" indicates identical or conserved residues in all to sequences in the alignment; a colon ":" indicates conserved substitutions; a period "." indicates semi-conserved substitutions; and a hyphen "-" indicates a gap in the sequence. The amino acid sequence predicted for the AviIII GH74 domain is approximately 46% identical to the *Aspergillus aculeatus* Avicelase III (endoglucanase) GH74 domain, indicating that the AviIII catalytic domain is a member of the GH74 family (Henrissat et al., 1991) supra).

TABLE 5

Multiple amino acid sequence alignment of a AviIII catalytic domain and polypeptides with Glycoside Hydrolase Family 74 catalytic domains.

```
GH74_Ace     ATTQPYTWSNVAIGGGG-FVDGIVFNEGAPGILYVRTDIGGMYRWDAANGRWIPLLDWVG
AviIII_Aac   AASQAYTWKNVVTGGGGGFTPGIVFNPSAKGVAYARTDIGGAYRLNSDD-TWTPLMDWVG
             *::*.***.**. ****  *. ***** .* *: *.****** **  ::  :   * **:****

GH74_Ace     WNNWGYNGVVSIAADPINTNKVWAAVGMYTNSWDPNDGAILRSSDQGATWQITPLPFKLG
AviIII_Aac   NDTWHDWGIDALATDPVDTDRVYVAVGMYTNEWDPNVGSILRSTDQGDTWTETKLPFKVG
             :.*   *: ::*:**::*::*:.******* **** *:****:*** **   * ****:*

GH74_Ace     GNMPGRGMGERLAVDPNNDNILYFGAPSGKGLWRSTDSGATWSQMTNFPDVGTYIANPTD
AviIII_Aac   GNMPGRGMGERLAVDPNKNSILYFGARSGHGLWKSTDYGATWSNVTSFTWTGTYFQDSSS
             *****************:.:****** **:***:*** *****:.*.*. .***: :..:

GH74_Ace     TTGYQSDIQGVVWVAFDKSSSSLGQASKTIFVGVADPNNPVFWSRDGGATWQAVPGAP-T
AviIII_Aac   T--YTSDPVGIAWVTFDSTSGSSGSATPRIFVGVADAGKSVFKSEDAGATWAWVSGEPQY
             *  * **  *:.**:**:**. :* * *.*:  *******...:.** *.*.****  *.* *

GH74_Ace     GFIPHKGVFDPVNHVLYIATSNTGGPYDGSSGDVWKFSVTSGTWTRISPVPSTDTANDYF
AviIII_Aac   GFLPHKGVLSPEEKTLYISYANGAGPYDGTNGTVHKYNITSGVWTDISP---TSLASTYY
             **:******:.*   :.***:  :.*  .*****:.* * *: :***.** ***    *. *. *:

GH74_Ace     GYSGLTIDRQHPNTIMVATQISWWPDTIIFRSTDGGATWTRIWDWTSYPNRSLRYVLDIS
AviIII_Aac   GYGGLSVDLQVPGTLMVAALNCWWPDELIFRSTDSGATWSPIWEWNGYPSINYYYSYDIS
             **.**.::* * *.*:***  : ****  :******* ****:  **:*. **     * ***

GH74_Ace     AEPWLTFGVQPNPPVPSPKLGWMDEAMAIDPFNSDRMLYGTGATLYATNDLTKWDSGGQI
AviIII_Aac   NAPWIQDTTSTDQFP--VRVGWMVEALAIDPFDSNHWLYGTGLTVYGGHDLTNWDSKHNV
             **:      ...:       : *** **:*****:*:: ***** *:*.   :****:***    ::

GH74_Ace     HIAPMVKGLEETAVNDLISPPSGAPLISALGDLGGFTHADVTAVPSTIFTSPVFTTGTSV
AviIII_Aac   TVKSLAVGIEEMAVLGLITPPGGPALLSAVGDDGGFYHSDLDAAPNQAYHTPTYGTTNGI
             :  .:. .*:** **  .**:**.*..*:**:** ***  *:*: *.*.   :  :*..:  *  ..:

GH74_Ace     DYAELNPSIIVRAGSFDPSSQPNDRHVAFSTDGGKNWFQGSEPGGVTTGGTVAASADGSR
AviIII_Aac   DYAGNKPSNIVRSGASDDYP-----TLALSSNFGSTWYADYAASTSTGTGAVALSADGDT
             ***  :** ***:*:*:  *        :*:*:: *..:*   :. ..   *   *:** ****.

GH74_Ace     FVWAPGDPGQPVVYAVGFGNSWAASQGVPANAQIRSDRVNPKTFYALSNGTFYRSTDGGV
AviIII_Aac   VLLMSSTSGALVSKSQG---TLTAVSSLPSGAVIASDKSDNTVFYGGSAGAIYVSKNTAT
             .:   ..  .* *  :*    :  * ..:*  ..*:*:..:**:.*  * * .:*  *.:   ..

GH74_Ace     TFQPVAAGLPSSGAVGVMFHAVPGKEGDLWLAASSGLYHSTNGGSSWSAI-TGVSSAVNV
AviIII_Aac   SFTKTVS-LGSSTTVNAIR-AHPSIAGDVWASTDKGLWHSTDYGSTFTQIGSSGVTAGWSF
             :*  ..: * ** :*...:  *  *. **:*  :::..**:***: ** :::  * :**::..  ..
```

TABLE 5 -continued

Multiple amino acid sequence alignment of a AviIII catalytic domain and polypeptides with Glycoside Hydrolase Family 74 catalytic domains.

```
GH74_Ace      GFGKSAPGSSYPAVFVVGTIGGVTGAYRSDDCGTTWVLINDDQHQYGN-WGQAITGDHAN
AviIII_Aac    GFGKASSTGSYVVIYGFFTIDGAAGLFKSEDAGTNWQVISDASHGFGSGSANVVNGDLQT
              ****::. .** .:: . **.*.:* ::*:*.**.* :*.* .* :*. .:::.** .

GH74_Ace      LRRVYIGTNGRGIVYGDIGGAPSG
AviIII_Aac    YGRVFRGHERPGHLLRQSQREPAG
              **: * : * : :    *:*
```

Multialignment of related Glycoside Hydrolase Family 74 catalytic domain
GH74_Ace: *Acidothermus cellulolyticus* AviIII catalytic domain GH74 (SEQ ID NO: 3)
AviIII_Aac: *Aspergillus aculeatus* Avicclase III (endoglucanase). GeneBank Acc. # BAA29031 (SEQ ID NO: 7)

Example 3

Mixed Domain GH74, CBD II, CBD III Genes and Hybrid Polypeptides

From the putative locations of the domains in the AviIII cellulase sequence given above and in comparable cloned cellulase sequences from other species, one can separate individual domains and combine them with one or more domains from different sequences. The significant similarity between cellulase genes permit one by recombinant techniques to arrange one or more domains from the *Acidothermus cellulolyticus* AviIII cellulase gene with one or more domains from a cellulase gene from one or more other microorganisms. Other representative endoglucanase genes include *Bacillus polymyxa* beta-(1,4) endoglucanase (Baird et al, Journal of Bacteriology, 172: 1576-86 (1992)) and *Xanthomonas campestris* beta-(1,4)-endoglucanase A (Gough et al, Gene 89:53-59 (1990)). The result of the fusion of any two or more domains will, upon expression, be a hybrid polypeptide. Such hybrid polypeptides can have one or more catalytic or binding domains. For ease of manipulation, recombinant techniques may be employed such as the addition of restriction enzyme sites by site-specific mutagenesis. If one is not using one domain of a particular gene, any number of any type of change including complete deletion may be made to in the unused domain for convenience of manipulation.

It is understood for purposes of this disclosure, that various changes and modifications may be made to the invention that are well within the scope of the invention. Numerous other changes may be made which will readily suggest themselves to those skilled in the art and which are encompassed in the spirit of the invention disclosed herein and as defined in the appended claims.

This specification contains numerous citations to references such as patents, patent applications, and publications. Each is hereby incorporated by reference for all purposes.

What is claimed is:

1. A method for degrading cellulose in a starting material, comprising treating the starting material with an isolated polypeptide comprising SEQ ID NO: 1 or comprising a fragment of SEQ ID NO: 1 having cellulase activity.

2. The method of claim 1, further comprising treating the starting material with a second glycoside hydrolase polypeptide.

3. The method of claim 1, wherein the starting material is biomass.

4. The method of claim 1, wherein the starting material is agricultural or forestry biomass.

5. The method of claim 1, wherein the starting material is municipal solid waste.

6. The method of claim 1, wherein the isolated polypeptide comprises SEQ ID NO:1.

7. The method of claim 1, wherein the starting material is treated at a temperature of about 15° C. to about 100° C.

8. The method of claim 1, wherein the starting material is treated at a temperature of about 30° C. to about 80° C.

9. The method of claim 1, wherein the starting material is treated at a temperature of about 50° C. to about 70° C.

10. The method of claim 9, wherein the starting material is treated at an acidic pH.

11. The method of claim 1, wherein the starting material is treated at an acidic pH.

12. The method of claim 1, wherein the ratio of polypeptide to starting material is about 1 to 50.

13. The method of claim 1, further comprising processing the starting material to reduce its size.

14. The method of claim 1, further comprising a step of treating the starting material with an acid before treatment with the isolated polypeptide.

15. A method for degrading cellulose in biomass, comprising treating the biomass with an isolated polypeptide, comprising SEQ ID NO: 1 or comprising a fragment of SEQ ID NO: 1 having cellulase activity, at a temperature of about 50° C. to about 70° C. and at an acidic pH.

16. The method of claim 15, further comprising a step of treating the biomass with an acid before treatment with the isolated polypeptide.

* * * * *